US006406891B1

(12) United States Patent
Legerski

(10) Patent No.: US 6,406,891 B1
(45) Date of Patent: Jun. 18, 2002

(54) DUAL RT PROCEDURE FOR CDNA SYNTHESIS

(75) Inventor: Randy John Legerski, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/162,631

(22) Filed: Sep. 28, 1998

(51) Int. Cl.$^7$ .............................. C12P 19/34; C12Q 1/68

(52) U.S. Cl. .......................... 435/91.1; 435/6; 435/91.2; 435/69.1; 435/320.1; 435/240.2; 435/440

(58) Field of Search .......................... 435/6, 91.1, 91.2, 435/69.1, 320.1, 240.2, 440

(56) References Cited

U.S. PATENT DOCUMENTS

| | | | |
|---|---|---|---|
| 5,310,652 A | | 5/1994 | Gelfand et al. ................. 435/6 |
| 5,641,864 A | * | 6/1997 | Gelfand ....................... 530/350 |

FOREIGN PATENT DOCUMENTS

| | | |
|---|---|---|
| EP | 0479158 | 9/1991 |
| WO | WO 94/05797 | 3/1994 |
| WO | WO 97/21821 | 6/1997 |

OTHER PUBLICATIONS

Adler and Modrich, "T7–induced DNA polymerase," *J. Biol. Chem.*, 254:11605–11614, 1979.
"Advantage® PCR Kits & Polymerase Mixes," from the internet at website: http://www.clontech.com/clontech/Catalog/PCR/Advantage.html. Undated.
"AmpliTaq DNA Polymerase and Native Taq DNA Polymerase: Selection Guide," from the internet at website: http://www2.perkin–elmer.com/pc/700905/content/selectionGuide.html. Undated.
Bebenek and Kunkel, "The use of native T7 DNA polymerase for site–directed mutagenesis," *Nucl. Acids Res.*, 17:5408, 1989.
Bentley et al., "The *schizosaccharomyces pombe* rad3 checkpoint," *EMBO J.* 15, 6641–6651, 1996.
Bicknell et al., "Selection for β$_2$–microglobulin mutation in mismatch repair–defective colorectal carcinomas," *Current Biology*, 6(12):1695–1697, 1996.
Bronner et al., "Mutation in the DNA mismatch repair gene homologue hMLH1 is associated with hereditary non–polyposis colon cancer," *Nature*, 368:258–261, 1994.
Buell et al., "Synthesis of full length cDNAs from from four partially purified oviduct mRNAs," *J. Biol. Chem.*, 253:2471–2482, 1978.
"CapFinder™ PCR cDNA Synthesis Kit: Generate high–quality cDNA for a wide spectrum of applications," from the internet at website: http://www.clontech.com/clontech/OCT96UPD/CapFinder.html. Undated.

Dale et al., "A rapid single–stranded cloning strategy for producing a sequential series of overlapping clones for use in DNA sequencing: application to sequencing the corn mitochondrial 18 S rDNA," *Plasmid*, 13:31–40, 1985.
Eckert and Kunkel, "DNA polymerase fidelity and the polymerase chain reaction," *PCR Methods and Applications*, 1:17–24, 1991.
Efstratiadis et al., "Enzymatic in vitro synthesis of globin genes," Cell 7:279–288, 1976.
Ender et al., "Overexpression of an elongation factor–1γ–hybridizing RNA in colorectal adenomas, " *Molecular Carcinogenesis*, 7:18–20, 1993.
Engler et al., "Two forms of the DNA polymerase of bacteriophage T7," *J. Biol. Chem.*, 258:11165–11173, 1983.
Fishel et al, "The human mutator gene homolog MSH2 and its association with hereditary nonpolyposis colon cancer," Cell, 75:1027–1038, 1993.
"GeneAmp EZ rTth RNA PCR Kit: Screening," from the internet at website: http://www2.perkin–elmer.com/pc/771903/content/screening.html. Undated.
"GeneAmp RNA PCR Core Kit: Economical," from the internet at website: http://www2.perkin–elmer.com/pc/771903/content/economical.html. Undated.
"GeneAmp RNA PCR Core Kit: Traditional," from the internet at website: http://www2.perkin–elmer.com/pc/771903/content/traditional.html. Undated.
"GeneAmp Thermostable rTth Reverse Transcriptase RNA PCR Kit: Powerful," from the internet at website: http://www2.perkin–elmer.com/pc/771903/content/powerful.html, Undated.
"GeneAmp XL RNA PCR Kit: Long RT PCR Products," from the internet at website: http://www2.perkin–elmer.com/pc/771520/content.html. Undated.
Glisin et al., "Ribonucleic acid isolated by cesium chloride centrifugation," *Biochem.*, 13:2633, 1974.
Grippo and Richardson, "Deoxyribonucleic acid polymerase of bacteriophage T7," *J. Biol. Chem.*, 246:6867–6873, 1971.
Gubler and Hoffmann, "A simple and very efficient method for generating cDNA libraries," *Gene*, 25:263–269, 1983.
Gubler, "[35] Second–strand cDNA synthesis: mRNA fragments as primers," *Methods Enzymol.*, 152:330–335, 1987.
Hearne et al., "Microsatellites for linkage analysis of genetic traits," *Trends Genet*, 8:288–94, 1992.
Henning et al., "The Cockayne Syndrome Group A gene encodes a WD repeat protein that interacts with CSB protein and a subunit of RNA polymerase II TFIIH," *Cell*, 82:555–564, 1995.

(List continued on next page.)

Primary Examiner—Jeffrey Fredman
(74) Attorney, Agent, or Firm—Fulbright & Jaworski, LLP

(57) ABSTRACT

The present invention provides methods and compositions for the synthesis of long cDNA species. More particularly the present invention employs cycling between a low temperature and a high temperature reverse transcriptase activity to bypass the problem of secondary structures. Also described are methods of producing cDNA libraries and RT-PCR procedures.

34 Claims, 2 Drawing Sheets

OTHER PUBLICATIONS

Hori et al., "Deoxyribonucleic acid polymerase of bacteriophage T7," *J. Biol. Chem.,* 254(22):11598–11604, 1979.

Houts et al., "Reverse transcriptase from avian myeloblastosis virus," *J. Virol.,* 29(2):517–522, 1979.

Griffin and Griffin (Eds.), In: *PCR Technology: Current Innovations,* CRC Press, Boca Raton, FL, pp 228–229, 1994.

Jannasch et al., "Comparative physiological studies on hyperthermophilic archaea isolated from deep–sea hot vents with emphasis on Pyrococcus strain GB–D,"*Applied Environ. Microbiol.,* 58(11):3472–3481, 1992.

Järvinen, "Epidemiology of familial adenomatous polyposis in Finland: impact of family screening on the colorectal cancer rate and survival," *Gut,* 33:357–360, 1992.

Jass and Stewart, "Evolution of hereditary non–polyposis colorectal cancer," *Gut,* 33:783–786, 1992.

Kong et al., "Characterization of a DNA polymerase from the Hyperthermophile Archaea *Thermococcus litoralis,*" *J. Biol. Chem.,* 268(3):1965–1975, 1993.

Kunkel et al., "Rapid and efficient site–specific mutagenesis without phenotypic selection," *Methods Enzymol.,* 154:367–382, 1987.

Lawyer et al., "Isolation, characterization, and expression in *Escherichia coli* of the DNA polymerase gene from *Thermus aquaticus,*" *J. Biol. Chem.,* 264(11):6427–6437, 1989.

Lawyer et al., "High–level expression, purification, and enzymatic characterization of full–length *Thermus aquaticus* DNA polymerase and a truncated form deficient in 5' to 3' exonuclease activity," *PCR Meth. Appl.,* 2(4):275–287, 1993.

Leach et al., "Mutations of a mutS homolog in hereditary nonpolyposis colorectal cancer," *Cell,* 75:1215–1225, 1993.

Leader et al., "Short Communication: Isolation and characterization of cDNA clones from mouse skeletal muscle in actin mRNA," *DNA,* 5(3):235–238, 1986.

Legerski and Robberson, "Analysis and optimization of recombinant DNA joining reactions," *J. Molec. Biol.* 181, 297–312, 1985.

Legerski, and Peterson, "Expression cloning of a human DNA repair gene involved in xeroderma pigmentosum group C," *Nature,* 359:70, 1992.

Lengauer et al., "Genetic instability incolorectal cancers," *Nature,* 386:623–626, 1997.

Liu et al., "Mismatch repair gene defects in sporadic colorectal cancers with microsatellite instability," *Nature Genetics,* 9:48–55, 1995.

Lu et al., "Large fragment of DNA Polymerase I from *Bacillus stearothermophilus* (Bst Polymerase) is stable at ambient temperature," *BioTechniques,* 11(4):464, 1991.

Lynch et al., "Differential diagnosis of hereditary nonpolyposis colorectal cancer (Lynch Syndrome I and Lynch Syndrome II)," *Dis. Col Rect,* 31:372–377; 1988.

Lynch et al., "Genetics, natural history, tumor spectrum, and pathology of hereditary nonpolyposis colorectal cancer: An updated review," *Gastroenterology;* 104:1535–1549, 1993.

Mallet et al., "Continuous RT–PCR using AMV–RT and Taq DNA polymerase: Characterization and comparison to uncoupled procedures," *BioTechniques,* 18(4):678–687, 1995.

Markowitz et al., "Inactivation of the Type II TGF–β receptor in colon cancer cells with microsatellite instability," *Science,* 268:1336–1338, 1995.

"MasterAmp™ RT–PCR Kit: Product Information," from the internet at website: http://www.epicentre.com/lit/martlit.htm. Undated.

Mattila et al., "Fidelity of DNA synthesis by the *Thermococcus litoralis* DNA polymerase—an extremely heat stable enzyme with proofreading activity," *Nucl. Acids Res.,* 19(18):4967–4973, 1991.

McClary et al., "Sequencing with the large fragmen of DNA polymerase I from *Bacillus stearothermophilus,*" *J. DNA Sequencing Mapping,* 1(3):173–180, 1991.

Mead et al., "Bst DNA polymerase permits rapid sequence analysis from nanogram amounts of template," *BioTechniques,* 11(1):76–87, 1991.

Meinkoth and Wahl, "Nick translation," *Methods Enzymol.,* 152:91–94, 1987.

Modrich and Richardson, "Bacteriophage T7 deoxyribonucleic acid replication in vitro," *J. Biol. Chem.,* 250(14):5515–5522, 1975.

"mRNA Isolation Kit," from the internet at website: http://www2.perkin–elmer.com/pc/771521/771521.html. Undated.

Mulvihill, Ingall, Mastromarino (Eds.), "The frequency of hereditary large bowel cancer," In: *Prevention of Hereditary Large Bowel Cancer,* Alan R. Liss, New York, pp 61–75, 1983.

Murray and Kelley, "Characterization of λ.polA transducing phages; effective expression of the *E. coli* polA gene," *Molec. Gen. Genet.,* 175:77–87, 1979.

Myers and Gelfand, "Reverse transcription and DNA amplification by a *Thermus thermophilus* DNA polymerase," *Biochemistry,* 30(31):7661–7666, 1991.

"Native Taq DNA Polymerase: The Original Thermostable DNA Polymerase," from the internet at website: http://www2.perkin–elmer.com/pc/700905/content/originalThermostable.html. Undated.

Nordström et al., "Characterization of bacteriophage T7 DNA polymerase purified to homogeneity by antithioredoxin immunoadsorbent chromatography," *J. Biol. Chem.,* 256(6):3112–3117, 1981.

Okayama and Berg, "High–efficiency cloning of full–length cDNA," *Mol. Cell. Biol.,* 2(2):161–170, 1982.

Papadopoulos et al., "Mutation of a mutL homolog in hereditary colon cancer," *Science,* 263:1625–1629, 1994.

Papadopoulos et al., "Mutations of GTBP in genetically unstable cells," *Science.* 268(5219): 1915–1917, 1995.

Perler et al., "Thermostable DNA polymerases," *Adv. Protein Chem.,* 48:377–435, 1996.

Perler et al., "Intervening sequences in an Archaea DNA polymerase gene," *Proc. Nat'l Acad. Sci. USA,* 89:5577–5581, 1992.

Peterson and Legerski, "High–frequency transformation of human repair–dificient cell lines by an Eptein–Barr virus–based cDNA expression vector," *Gene,* 107:279–284, 1991.

Powell et al., "APC mutations occur early during colorectal tumorigenesis," *Nature,* 359:235–237, 1992.

Quirke et al., DNA aneuploidy and cell proliferation in familial adenomatous polyposis, *Gut,* 29:603–607, 1988.

Rampino et al., "Somatic frameshift mutations in the BAX gene in colon cancers of the microsatellite mutator phenotype," *Science,* 275(5302):967–969, 1997.

"RNA PCR Kits/EZ: GeneAmp™ EZ rTth RNA PCR Kit," from the internet at website: http://www2.perkin–elmer.com/pc/catalog2/pg16.html). Undated.

"rTth DNA Polymerase: For RNA PCR," (from the internet at website: http://www2.perkin-elmer.com/pc/700905/content/forRNApcr.html Undated.

Sanger et al., "DNA sequencing with chain-terminating inhibitors," *Proc. Nat'l Acad. Sci. USA,* 74(12):5463–5467, 1977.

Savitsky et al., "A single ataxia teleangiectasia gene with a product similar to PI–3 kinase," *Science,* 268:1749–1753, 1995.

Savitsky et al., "The complete sequence of the coding region of the ATM gene reveals similarity to cell cycle regulators in different species," *Hum. Mol. Genet.,* 4(11):2025–2032, 1995.

Schwabe et al., "ThermoScript™ RT, a new avian reverse transcriptase for high-temperature cDNA synthesis to improve RT–PCR," *Focus,* 20(2):30–33, 1998.

Shimomaye and Salvato, "Use of avian myeloblastosis virus reverse transcriptase at high temperature for sequence analysis of highly structured RNA," *Gene Anal. Techn.,* 6:25–28, 1989.

Souza et al., "Microsatellite instability in the insulin–like growth factor II receptor gene in gastrointestinal tumours," *Nature Genetics,* 14:255–257, 1996.

Studier et al., "Use of T7 RNA polymerase to direct expression of cloned genes," *Methods Enzymol.,* 185:60–89, 1990.

Tabor and Struhl, In: *Current Protocols in Molecular Biology,* Ausubel et al. (Eds.), John Wiley and Sons, NY, pp 3.5.10–3.5.12, 1987.

Tebbs et al., "Correction of chromosomal instability and sensitivity to diverse mutagens by a cloned cDNA of the XRCC3 DNA repair gene," *Proc. Natl. Acad. Sci., U.S.A.,* 92:6354–6358, 1995.

Tellier et al., "Amplification of the full-length hepatitis A virus genome by long reverse transcription–PCR and transcription of infectious RNA directly from the amplicon," *Proc. Natl. Acad. Sci. USA,* 93:4370–4373, 1996.

"ThermoScript™ RT–PCR System," Catalog No. 11146–106. Undated.

Thibodeau et al., "Microsatellite instability in cancer of the proximal colon," *Science,* 260:816–819, 1993.

Ullrich et al., "Rat insulin genes: construction of plasmids containing the coding sequences," *Science,* 196:1313–1318, 1977.

"UlTma DNA Polymerase: A Proofreading Enzyme," from the internet at website: http://www2.perkin-elmer.com/pc/700905/content/proofreadingEnzyme.html.,Undated.

"UperScript™ RNase H: Reverse Transcriptase," Catalog No. 18053–017. Undated.

Villani et al., "Elongation of RNA–primed DNA templates by DNA polymerase α from *Drosophila melanogaster* embryos," *J. Biol. Chem.,* 256(15):8202–8207, 1981.

Wei et al., "Simultaneous amplification of four DNA repair genes and β–actin in human lymphocytes by multiplex reverse transcriptase–PCR," *Cancer Res.,* 55(21):5025–5029, 1995.

Wei et al., "Expression of five selected human mismatch repair genes simultaneously detected in normal and cancer cell lines by a nonradioactive multiplex reverse trasncription–polymerase chain reaction," *Pathobiology,* 65(6):293–300, 1997.

Weber, "Informativeness of human $(dC-dA)_n \cdot (dG-dT)_n$ polymorphisms," *Genomics,* 7:524–530, 1990.

Young et al., "Detection of hepatitis C virus RNA by a combined reverse transcription–polymerase chain reaction assay," *J. Clin. Microbiol.,* 31(4):882–886, 1993.

Carninci et al, "Thermostabilization and thermoactivation of thermolabile enzymes by trehalose and its application for the synthesis of full length cDNA", Proc. Natl. Acad. Sci. (Jan. 1998) 95:520–524.*

Cunningham et al, "Molecular genetic basis of colorectal cancer susceptibility", British J. Surgery (1996) 83:321–329.*

Ambion Catalog (1993/1994) p. 60.*

* cited by examiner

Human ataxia-telangiectasia (ATM) cDNA

DUAL RT PROCEDURE FOR CDNA SYNTHESIS

BACKGROUND OF THE INVENTION

1. Field of the Invention

The present invention relates generally to the field of molecular biology. More particularly, the present invention provides an improved reverse transcription method that allows the synthesis of long cDNA species.

2. Description of Related Art

A number of methods have been employed over the years for the synthesis of complementary DNA (cDNA). All of these methods utilize a reverse transcriptase (RT) for first strand synthesis and either a DNA polymerase or reverse transcriptase for second strand synthesis.

One of the first methods for isolating high quality cDNA was described by Efstratiadis et al. (1976). These investigators took advantage of the fact that, for reasons not completely understood, a small percentage of single-stranded cDNA will form hairpin structures at their 3' ends. The hairpin structure could be used for priming of second strand synthesis and the hairpin was subsequently digested by S1 nuclease prior to cloning into a vector. Insertion into the vector was accomplished by using terminal transferase to form complementary homopolymeric tails at the ends of the vector and the cDNA. Despite the usefulness of this approach there were several drawbacks. It was not clear that all cDNAs formed hairpin structures and thus these libraries may not have been completely representational. Also, some degradation of the cDNA may result from the S1 nuclease digestion.

A major advance in the preparation of cDNA was the replacement synthesis method for second strand synthesis first introduced by Okayama and Berg (1982) and later modified by Gubler and Hofiman (1983). In this method, the second strand is synthesized by a nick translation procedure in which the mRNA strand is nicked by RNase H producing primers that can be utilized by *E. coli* polymerase I. This method is very efficient and eliminates the need for a S1 nuclease reaction. It remains the method of choice for second strand cDNA synthesis. For first strand synthesis, the enzymes primarily used have been either from the Moloney Murine Leukemia Virus (MMLV) or the avian myeloblastosis virus (AMV). The AMV RT was somewhat preferred because its optimum temperature was 42° C. compared to 37° C. for the MMLV enzyme. However, recently, the MMLV gene has been mutated in order to eliminate the endogenous RNase H activity, and this modified enzyme referred to as Superscript RT (Gibco-BRL), is superior for the production of full-length cDNAs.

A major impediment to the production of full-length cDNAs by existing techniques has been the occurrence of secondary structure in the mRNA. These and perhaps other naturally occurring pause sites inhibit the progression of the reverse transcriptases, and thus prevent the synthesis of full-length first strand cDNA. A number of methods, including the use of methylmercury hydroxide to denature the mRNA, have been used to remove the secondary structure during first strand synthesis. However, these methods have not proven to be completely satisfactory. Methylmercury hydroxide, for example, in addition to being highly toxic, inhibits RTs to some extent.

Another method for eliminating secondary structure in mRNA is to perform first strand synthesis at higher temperatures. However, this method also is flawed because the half lives of the MMLV and AMV enzymes at high temperatures are significantly reduced. Recently, however, RTs that are active at extremely high temperatures have been isolated. Unfortunately, such enzymes are not highly processive and therefore are not sufficient for the synthesis of full-length first strand cDNA.

An expression cloning approach that utilized an Epstein-Barr virus-based cloning vector capable of replicating extrachromasomally in human cells has been attempted to produce long cDNAs. The pEBS7 vector could be used for the efficient transformation and expression of cDNAs in human cells (Peterson and Legerski, 1991). Using a library prepared from mRNA derived from HeLa cells, the inventor's group was able to initially clone the gene that complements the xeroderma pigmentosum group C (XPC) gene (approximately 4 kb) (Legerski and Peterson, 1992). In addition, the cloning of the Cockayne's syndrome group A (CSA) gene (Tebbs et al., 1995), and a gene, XRCC3, that complements a Chinese hamster ovary (CHO) DNA repair mutant (Henning et al., 1995) also was achieved. Furthermore, two additional genes, XRCC2 and XRCC9, that complement CHO DNA repair mutants, have been cloned using the pEBS7 libraries.

Despite these successes, it remains apparent that very long cDNAs, above five or six kb, still were not well represented in these libraries. All of the genes discussed above were four kb or less in length. Attempts to clone longer gene sequences by this method have been unsuccessful. This defines a deficiency in the art in the production of full length cDNAs that has yet to be addressed.

SUMMARY OF THE INVENTION

In a particular embodiment, the present invention provides a method for the synthesis of cDNA comprising the steps of (a) providing a reaction mixture comprising a poly (A)+RNA, an oligonucleotide primer, dNTPs, (b) incubating the reaction mixture of step (a) with a highly processive enzyme composition having reverse transcriptase activity and incubating the reaction mixture at a normal temperature range to allow first strand synthesis; (c) incubating the reaction mixture of step (b) with a thermostable enzyme composition having reverse transcriptase activity and incubating the reaction mixture at a temperature that inhibits the presence of secondary mRNA structures to generate a first strand; (d) adding the first strand to a reaction mixture for the synthesis of a second strand complementary to the first strand wherein the second strand synthesis reaction mixture comprises dNTPs and a DNA polymerase to initiate synthesis of the second strand and incubating the reaction mixture under conditions to allow the formation of a double-stranded cDNA. In specific embodiments, steps b and c are repeated. Steps b and c may be repeated once, twice, three, four or more times. More particularly, steps b and c are repeated until the appropriate length of first strand of the cDNA is generated.

In specific embodiments, the reaction mixture of step (a) further may comprise an RNase inhibitor. In other embodiments, the second strand synthesis reaction mixture of step (d) further comprises DEPC-treated H20. In still further embodiments, the second strand synthesis reaction mixture of step (d) further comprises RNase H. Certain embodiments further comprise the step of amplifying the double-stranded cDNA molecule of step (d). More particularly, the step of amplifying comprises PCR.

In specific embodiments, the temperature of step (b) is between about 37° C. and about 43° C. In other embodiments, the temperature of step (c) about 56° C. and about 95° C. The temperature in step (b) will be the temperature range optimal for any processive RT enzyme. The temperature range in step (c) will be any temperature range optimal for a thermostable RT. In specific examples, the processive reverse transcriptase may be selected from the group consisting of Superscript™; AMV Reverse Transcriptase, M-MLV Reverse Transcriptase. In particular examples, the thermostable reverse transcriptase is selected from the group consisting of Retrotherm™; Thermoscript™ and Tth reverse transcriptase.

In other embodiments, it is envisioned that the DNA polymerase is thermostable or non-thermostable. The DNA polymerase may be selected from the group consisting of DNA Polymerase I, T4 DNA Polymerase, DNA Polymerase I Klenow fragment, PLATINUM taq™. More particularly, the thermostable DNA polymerase may be selected from the group consisting of Tfl DNA Polymerase, Taq DNA Polymerase, Tli DNA Polymerase, Tth DNA Polymerase, Vent™, Deepvent™ and pfu.

In particularly defined embodiments, the sample comprises between about 0.1 and picograms and 10 micrograms of polyA RNA. Of course this is an exemplary range and other ranges of polyA RNA also are contemplated for example from about 1 picogram to about 1 microgram; 10 picograms to about 900 nanograms; 20 picograms to about 800 nanograms; 30 picograms to about 700 nanograms; 40 picograms to about 600 nanograms; 50 picograms to about 500 nanograms; 60 picograms to about 400 nanograms; 70 picograms to about 300 nanograms; 80 picograms to about 200 nanograms. It will be understood by those of skill in the art that virtually any amount of polyA RNA may be present in the sample. Also it is contemplated that the RNA may be total RNA extract from a tissue. In particular embodiments, it is contemplated that the poly(A)+RNA is from a tumor. In specific embodiments it is contemplated that the reaction mixture comprises between 1 and $10^8$ copies of the poly (A)+RNA. Any number of copies between this range also is specifically contemplated.

In specific embodiments, the method may further comprise the step of adding linkers to the double stranded cDNA. More particularly, the linkers are added by blunt end ligation.

Also contemplated is a method of increasing the length of cDNAs in a cDNA library comprising the steps of (a) providing a reaction mixture comprising a poly (A)+RNA, an oligonucleotide primer and dNTPs, (b) incubating the reaction mixture of step (a) with a highly processive enzyme composition having reverse transcriptase activity and incubating the reaction mixture at a normal temperature range to allow first strand synthesis; (c) incubating the reaction mixture of step (b) with a thermostable enzyme composition having reverse transcriptase activity and incubating the reaction mixture at a temperature that inhibits the presence of secondary mRNA structures to generate a first strand; (d) adding the first strand to a reaction mixture for the synthesis of a second strand complementary to the first strand wherein the second strand synthesis reaction mixture comprises dNTPs and a DNA polymerase to initiate synthesis of the second strand and incubating the reaction mixture under conditions to allow the formation of double-stranded cDNA, and (e) amplifying the double-stranded cDNA of step (d); wherein incubation at the temperatures in steps (c) inhibits the formation of secondary mRNA structures thereby resulting in cDNA species that are longer than in those produced in a normal temperature range.

Another embodiments contemplates a method for the production of full length cDNAs comprising the steps of (a) providing a reaction mixture comprising a poly (A)+RNA, an oligonucleotide primer and dNTPs; (b) incubating the reaction mixture of step (a) with a highly processive enzyme composition having reverse transcriptase activity and incubating the reaction mixture at a normal temperature range to allow first strand synthesis; (c) incubating the reaction mixture of step (b) with a thermostable enzyme composition having reverse transcriptase activity and incubating the reaction mixture at a temperature that inhibits the presence of secondary mRNA structures to generate a first strand; (d) adding the first strand to a reaction mixture for the synthesis of a second strand complementary to the first strand wherein the second strand synthesis reaction mixture comprises dNTPs and a DNA polymerase to initiate synthesis of the second strand and incubating the reaction mixture under conditions to allow the formation of a double-stranded cDNA molecule, and (e) amplifying the double-stranded cDNA molecule of step (d) wherein the inhibition of secondary structure formation in step (b) allows the production of long cDNA moieties.

In specific embodiments, the cDNA moiety has a size of between about 0.5 kB and 20 kB. Of course this is an exemplary size range, the present invention is directed towards providing a method of making cDNA by reverse transcription such that the secondary structures in RNA transcripts do not interfere with the elongation of the first strand of cDNA. The cDNA may be 0.5 kb, 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb or larger.

In specific embodiments, the ADNA encodes a gene selected from the group consisting of XPC, CSA, XRCC3, XRCC2, XRCC9, ATM, ATR, RAD3), DNA-PK, ERCC1, XPA, XPB, XPC, XPD, XPF, XPQ, CSB and HHR23B. In other embodiments, the cDNA encodes a gene related to colorectal carcinoma. More particularly, the colorectal carcinoma is hereditary colorectal carcinoma. In other embodiments, the colorectal carcinoma is sporadic colorectal carcinoma. In those embodiments in which the cancer is a hereditary colorectal carcinoma the gene may be selected from the group consisting of hMSH2, hMLH1, hPMS1, hPMS2 and GTBP. In those embodiments in which the colorectal carcinoma is sporadic colorectal carcinoma the gene may be selected from the group consisting of transforming growth factor b type II receptor, insulin-like growth factor II receptor, BAX and β2-microglobulin.

Also provided herein is a method for synthesizing long cDNA moieties comprising the steps of (a) providing a reaction mixture comprising a poly (A)+RNA, an oligonucleotide primer and dNTPs, (b) incubating the reaction mixture of step (a) with a highly processive enzyme composition having reverse transcriptase activity and incubating the reaction mixture at a normal temperature range to allow first strand synthesis; (c) incubating the reaction mixture of step (b) with a thermostable enzyme composition having reverse transcriptase activity and incubating the reaction mixture at a temperature that inhibits the presence of secondary mRNA structures to generate a first strand; (d) adding the first strand to a reaction mixture for the synthesis of a second strand complementary to the first strand wherein the second strand synthesis reaction mixture comprises dNTPs and a DNA polymerase to initiate synthesis of the second strand and incubating the reaction mixture under conditions to allow the formation of a double-stranded cDNA, and (e) amplifying the double-stranded cDNA molecule of step (d); wherein the inhibition of secondary structure formation in step (b) allows the production of cDNA moieties that are longer than those obtained when such secondary structure formation is not inhibited.

Another embodiment provides a method for producing a library of cDNA species from a tumor comprising the steps of (a) providing a reaction mixture comprising a poly (A)+RNA extracted from the tumor, an oligonucleotide primer and dNTPs; (b) incubating the reaction mixture of step (a) with a highly processive enzyme composition having reverse transcriptase activity and incubating the reaction mixture at a normal temperature range to allow first strand synthesis; (c) incubating the reaction mixture of step (b) with a thermostable enzyme composition having reverse transcriptase activity and incubating the reaction mixture at a temperature that inhibits the presence of secondary mRNA structures to generate a first strand; (d) adding the first strand to a reaction mixture for the synthesis of a second strand complementary to the first strand wherein the second strand synthesis reaction mixture comprises dNTPs and a DNA polymerase to initiate synthesis of the second strand and incubating the reaction mixture under conditions to allow the formation of a double-stranded cDNA, and (e) amplifying the double-stranded cDNA molecule of step (d) and (f) inserting the cDNA into an appropriate vector. In specific embodiments, the tumor is a colorectal tumor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Location with regard to the ATM cDNA of PCR primers used in the analysis of cDNA synthesis. The arrow to the right indicates the start of first strand cDNA synthesis. (FIG. 1B) PCR analysis of the ATM gene after first strand synthesis. The numbers above the lanes refer to the number of cycles performed with the RTs. M indicates the marker lane. The primer set used to produce the PCR product is indicated to the right of the gel. Note that the product obtained with the A primer set increases with each cycle.

DESCRIPTION OF ILLUSTRATIVE EMBODIMENTS

Figure 1A:
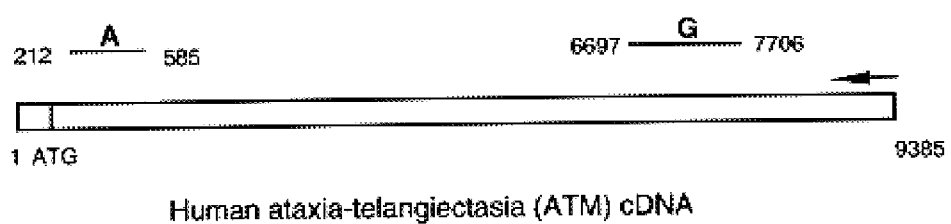
FIG. 1A and FIG. 1B Results from the dual RT cycling procedure for cDNA synthesis of the ATM gene.

Reverse transcription (RT) PCR, also called RNA PCR, has proven invaluable for detection and analysis of gene expression, RNA viruses, and generation of cDNAs for cloning. The process requires the reverse transcription of RNA to cDNA and subsequent amplification of the resultant cDNA using the polymerase chain reaction (PCR) process. Nevertheless, there is a problem with the existing techniques, in that these techniques can not produce cDNA moieties above five or six kb. This is due to the occurrence of secondary structures in the mRNA. These secondary structures inhibit the progression of the reverse transcriptases and thus prevent the synthesis of full-length first strand cDNA.

A. The Present Invention

As described more completely below, the present invention provides a method of producing full length first strand synthesis of cDNA. More particularly, the invention describes a method in which cycling back and forth between a processive RT and a thermostable RT enzyme during first strand synthesis allows for the complete production of the first strand of a full length cDNA. This invention exploits the notion that the mRNA secondary structures may be removed by elevating the temperature of the RT reaction. It is possible to carry out an RT reaction at the elevated temperatures using a thermostable RT enzymes, however, although these enzymes are operative at high temperatures (55–90°), the reaction is very slow. This inefficiency can be circumvented by adding fresh processive RT enzyme once the impediment of the secondary structure has been bypassed. Thus, the synthesis of the first strand can be continued at the lower temperature. This cycling allows the alternate synthesis of the long chain at the lower temperature and removal of the secondary structures at the higher temperature.

More particularly, the inventor has demonstrated that cycling back and forth between a processive RT enzyme and a thermostable RT enzyme allows the synthesis of long pieces of cDNA. By "processive RT enzyme" the present invention refers to any RT that is operative at a "normal" temperature. Such a normal temperature generally will fall within the range of between about 37° C. and about 45° C. This is the general temperature range of AMV RT and MMLV RT, and these enzymes have been shown to produce little or no full length product above 42° C. (Schwabe el al., 1998).

Thermostable RT enzymes, have a higher optimum temperature of operation than that of standard temperature RT enzymes. These enzymes are found to be active at temperatures ranging from about 55° C. to about 95° C. One of these thermostable enzymes, referred to as Retrotherm™ RT (Epicentre Technologies), is derived from a thermophilic bacterium and has a half-life of one hour at 95° C. and is fully active above 65° C. Unfortunately, the Retrotherm enzyme is not a highly processive enzyme and is thus not sufficient for the synthesis of full-length first strand cDNA by itself.

Thus, by exploiting a combination of (a) processive enzymes at a lower temperature to increase the length of the first strand of the cDNA and (b) thermostable enzymes at a higher temperature to remove the secondary structures formed in the first strand, the present invention provides an effective method of producing long cDNA moieties in an reverse transcription-based synthesis method. The specifics of the methods and compositions involved in this invention are described in further detail herein below.

In addition to developing new procedures for the preparation of full-length cDNA the present invention provides methods for the preparation of cDNA libraries from mRNA derived from tumors and their corresponding normal tissue. Tumors of breast, prostate, colon, and lung are of particular interest.

B. Enzymes and Reagents

The present section provides examples of enzymes and reagents used in the present invention to carry out reverse transcription, these include RT enzymes, DNA polymerases, RNase inhibitors and other compositions required or helpful for optimizing reaction conditions. Of course, the enzymes and reagents discussed below are exemplary and it is understood that any additional enzymes or reagents that possess similar activities may substitute for those specifically described.

a. Reverse Transcriptases

The present invention employs two different reverse transcriptases for the first strand synthesis of cDNAs. The methods of the present invention allow the circumvention of the problems created by mRNA secondary structures that form at the normal operating ranges of the reverse transcription reaction. As stated earlier, the normal operating range of RT enzymes is between about 37° C. and about 45° C. In order to inhibit, prevent or remove the formation of such secondary structures, the methods of the present invention involve cycling between normal temperature ranges and high temperature ranges.

At the normal temperature ranges, standard RT enzymes exhibit processive activity that efficiently produces the second strand but for the presence of secondary structure (www.perkin-elmer.com/pc/771903/content/powerful.html; Wickens el al., 1978; Shimoomaye et al., 1989). At this point, the addition of a thermostable RT enzyme allows the synthesis of the first strand of the cDNA at elevated temperatures between about 55° C. and 95° C. Elevating the reaction mixture temperature to such a range reduces secondary structure inhibition of cDNA synthesis, thus the increased temperatures break down, inhibits, or otherwise abrogates the formation of the secondary structure.

The problem with carrying out an RT reaction to significantly elongate a first strand of cDNA at such elevated temperatures is that the reaction is very slow and even though these enzymes are thermostable, they are active for a period of only about an hour at such elevated temperatures. Thus, for long cDNA chain synthesis, the fast processive activity of the standard RT enzymes is necessary to produce the lengths required. Thus, once the secondary structure has been removed or bypassed using the elevated reaction temperature at which the thermostable RT enzymes operates, the temperature may be reduced to the normal processive temperature range and fresh standard processive RT may be added to elongate the chain. This cycle may be repeated 1, 2, 3, 4, 5, 6, 7, 8, 9, 10 or more times until the desired length of the first strand is generated. Of course, although it is convenient that the same processive RT and thermostable RT combination is used in these subsequent cycles, it is by no means a requisite that the same combination be used. Indeed, it may prove useful change the combinations of processive to thermostable enzymes. The present section describes a variety of processive and thermostable reverse transcriptases for use in the present invention.

i. Processive RTs

Processive RT enzymes are those enzymes that perform reverse transcription of RNA to the first strand of cDNA. Traditionally, such RT enzymes include MMLV RT, AMV RT and various others. More recently, certain processive enzymes have been developed that possess is superior for the production of full-length cDNAs, even at the lower temperature ranges. For example, the MMLV gene has been mutated in order to eliminate the endogenous RNase H activity and this modified enzyme referred to as Superscript RT (Gibco-BRL) is superior for the production of full-length cDNAs. These and other processive RT enzymes are described in further detail in the present section.

M-MLV Reverse Transcriptase. M-MLV (Moloney Murine Leukemia Virus Reverse Transcriptase) is an RNA-dependent DNA polymerase requiring a DNA primer and an RNA template to synthesize a complementary DNA strand. The enzyme is a product of the pol gene of M-MLV and consists of a single subunit with a molecular weight of 71 kDa. M-MLV RT has a weaker intrinsic RNase H activity than Avian Myeloblastosis Virus (AMV) reverse transcriptase which is important for achieving long full-length complementary DNA (<7 kB).

M-MLV can be use for first strand cDNA synthesis and primer extensions. Storage recommend at −20° C. in 20 mM Tris-HCl (pH 7.5), 0.2M NaCl, 0.1 mM EDTA, 1 mM DTT, 0.01% Nonidet® P-40, 50% glycerol. The standard reaction conditions are 50 mM Tris-HCl (pH 8.3), 7 mM $MgCl_2$, 40 mM KCl, 10 mM DTT, 0.1 mg/ml BSA, 0.5 mM $^3$H-dTTP, 0.025 mM oligo(dT)$_{50}$, 0.25 mM poly(A)$_{400}$ at 37° C.

M-MLV Reverse Transcriptase, Rnase H Minus. This is a form of Moloney murine leukemia virus reverse transcriptase (RNA-dependent DNA polymerase) which has been genetically altered to remove the associated ribonuclease H activity (Tanese and Goff, 1988). It can be used for first strand cDNA synthesis and primer extension. Storage is at 20° C. in 20 mM Tris-HCl (pH 7.5), 0.2M NaCl, 0.1 mM EDTA, 1 mM DTT, 0.01% Nonidet(® P-40, 50% glycerol.

AMV Reverse Transcriptase. Avian Myeloblastosis Virus reverse transcriptase is a RNA dependent DNA polymerase that uses single-stranded RNA or DNA as a template to synthesize the complementary DNA strand (Houts et al, 1979). It has activity at high temperature (42° C. −50° C.). This polymerase has been used to synthesize long cDNA molecules.

Reaction conditions are 50 mM Tris-HCl (pH 8.3), 20 mM KCl, 10 mM $MgCl_2$, 500 $\mu$M of each dNTP, 5 mM dithiothreitol, 200 $\mu$g/ml oligo-dT$_{(12-18)}$, 250 $\mu$g/ml polyadenylated RNA, 6.0 pMol $^{32}$P-dCTP, and 30 U enzyme in a 7 $\mu$l volume. Incubate 45 min at 42° C. Storage buffer is 200 mM $KPO_4$ (pH 7.4), 2 mM dithiothreitol, 0.2% Triton X-100, and 50% glycerol. AMV may be used for first strand cDNA synthesis, RNA or DNA dideoxy chain termination sequencing, and fill-ins or other DNA polymerization reactions for which Klenow polymerase is not satisfactory (Maniatis et al., 1976).

Superscript™ II RNase H- Reverse Transcriptase (U.S. Pat. No. 5,244,797, incorporated herein by reference) is purified to near homogeneity from *E. coli* containing the pol gene of Moloney Murine Leukemia Virus. The enzyme is used to synthesize first strand cDNA and will generally give higher yields of cDNA and more full length product than other reverse transcriptases.

An exemplary RT PCR that employs SUPERSCRIPT™ can be found in the Gibco catalog. Briefly, a 20-$\mu$l reaction volume can be used for 1–5 $\mu$g of total RNA or 50–500 ng of mRNA. The following components are added to a nuclease-free microcentrifuge tube:1 $\mu$l Oligo (dT)12–18 (500 $\mu$g/ml) 1–5 $\mu$g total RNA, sterile, distilled water to 12 $\mu$l. The reaction mixture is heated to 70° C. for 10 min and quickly chilled on ice. The contents of the tube are collected by brief centrifugation. To this precipitate is added: 4 $\mu$l 5×First Strand Buffer, 2 $\mu$l 0.1 M DTT, 1 $\mu$l 10 mM dNTP Mix (10 mM each dATP, dGTP, dCTP and dTTP at neutral pH). The contents are mixed gently and incubate at 42° C. for 2 min. Then 1 $\mu$l (200 units) of Superscript II™ is added and the reaction mixture is mixed by pipetting gently up and down. This mixture is then incubated for 50 min at 42° C. and then inactivated by heating at 70° C. for 15 min. The cDNA can now be used as a template for amplification in PCR. However, amplification of some PCR targets (those >1 kb) may require the removal of RNA complementary to the cDNA. RNA complementary to the cDNA may be removed by adding 1 μl (2 units) of *E. coli* RNase H and incubating at 37° C. for 20 min.

ii. Thermostable Rts

Recently, thermostable RT enzymes have been developed from various sources. Thermostable enzymes are those enzymes that perform reverse transcription of RNA to the first strand of cDNA at temperatures higher than those used by standard RT enzymes. There are a number of RT enzymes that have temperature optima that range from between about 55° C. to about 90° C. For example, RetroAmp™ is operative at temperatures of 70° C. and above. This and other thermostable RT enzymes are described in further detail in the present section.

Retrotherm™ RT (Epicentre technologies) is a thermostable reverse transcriptase and DNA polymerase derived from a thermophilic bacterium. This thermostable enzyme has both RNA- and DNA-dependent DNA polymerase activities under the same reaction conditions. These characteristics enable researchers to synthesize both strands of a specific cDNA in a single tube with no buffer changes. The only components need are Retrotherm RT, the Retrotherm Reaction Buffer supplied with the enzyme, deoxynucleoside-triphosphates (dNTPs), an RNA template, and specific primers for synthesis of each strand of cDNA. After first-strand synthesis, the RNA:DNA hybrid is thermally denatured to allow the second-strand primer to hybridize to the cDNA for second-strand synthesis in the same buffer. The high reaction temperatures possible with Retrotherm RT minimize secondary structure in templates. Thus, when primers are available for both strands, single-tube cDNA synthesis with Retrotherm RT is easy, fast and powerful, even when working with mixed populations of RNA. Retrotherm RT has no Rnase H activity.

If specific primers are available for priming synthesis of both cDNA strands from a target RNA, then single-tube cDNA synthesis with Retrotherm RT is fast and convenient, even when working with mixed populations of RNA. In these cases, the enzyme's thermostability and its combination of RNA- and DNA-dependent DNA polymerase activities that function well in the same buffer give Retrotherm RT a large advantage over other reverse transcriptases.

The amount of RNA needed depends on the application and whether the sample consists of a single RNA species or a mixture of different RNAs. Similarly, the optimal enzyme concentration will vary with the amount and nature of the template. A typical 50μl reaction contains 0.5 to 5.0 units of Retrotherm RT. Insufficient enzyme may fail to produce full-length product. Excess enzyme may result in failure to produce discrete bands. Two templates of the same size but differing in sequence, or different amounts of the same template, may have different optimal enzyme concentrations.

RetroAmp™. RetroAmp™ RT DNA Polymerase (Epicentre Technologies), is a highly efficient, thermally stable enzyme. The use of a thermal stable polymerase allows reverse transcription to take place at an elevated temperature, minimizing the effects of RNA secondary structure. RetroAmp™ is available in a commercial preparation with a 10×PCR Enhancer (with betaine) referred to as MasterAmp™. The presence of betaine (trimethyl glycine) in the MasterAmp 10×PCR Enhancer substantially improves the yield and specificity of amplification of many target sequences, especially those containing a high G+C content or secondary structure. Betaine lowers the melting temperature of G+C rich regions to a temperature more similar to A+T(U) rich regions. This results in destabilization of double-stranded regions which limits polymerase pausing, thereby increasing the yield of full-length product. In addition, betaine also may enhance PCR by protecting DNA polymerases from thermal denaturation.

Typically in the RT-PCR reaction, 50 μl reactions are assembled on ice as two separate 25 μl premixes and combined just before the reverse transcription step to minimize RNA sample degradation. One premix includes the dNTPs, primers, and the RNA template. The other premix included all other reaction components. The reactions contain 1×RT-PCR Buffer that comprises 3.0 mM $MgCl_2$, 1× MasterAmp PCR Enhancer, 0.5 mM $MnSO_4$, 400 μM each dNTP, 12.5 pmoles of each primer, 100 ng of total RNA template, and 2.5 units of RetroAmp™ RT DNA Polymerase. Standard reactions are incubated at 60° C. for 20 minutes for first strand cDNA synthesis, followed by 30–35 cycles of PCR. Annealing temperatures vary depending on the primer pair used; typically samples are denatured at 92° C. for 30 seconds, annealed at 60° C. for 30–60 seconds, and extended at 72° C. for 60 seconds. Ten percent of each reaction (5 μl) may be separated by agarose gel electrophoresis and visualized with ethidium bromide staining.

RetroAmp™ RT DNA Polymerase can efficiently reverse transcribe RNA into cDNA at the highest temperatures possible. In the manufacture's specification the ability of RetroAmp™ RT DNA Polymerase to perform high-temperature RT-PCR, is demonstrated by performing RT-PCR using four different first-strand synthesis incubation temperatures (55° C., 60° C., 65° C., and 70° C.) with two different templates. Primers that amplify a 479 bp region of *E. coli* 16S rRNA were used in a standard reaction with the following cycling conditions: RNA was reverse transcribed at the specified temperature for 20 minutes, then 20 cycles of 92° C. for 30 seconds and 68° C. for 60 seconds were performed. Primers that amplify a 250 bp region of the [beta]-actin message from human placental RNA were also used in a standard reaction with the following cycling profile: RNA was reverse transcribed at the specified temperature for 20 minutes, then 35 cycles of 92° C. for 40 seconds and 70° C. for 60 seconds were performed. (These high annealing temperatures were possible because of the primer sequences chosen and the optimized buffer conditions used, including the presence of MasterAmp PCR Enhancer.) The 16S rRNA product is optimally amplified with a reverse transcription temperature of 65° C. and the [beta]-actin message amplifies well under all temperatures tested. The RetroAmp™ RT-PCR produces abundant specific products with reverse transcription temperatures up to 70° C., depending on the primer sequences and template abundance in the reaction.

Thermoscript™ Thermoscript™ (Gibco-BRL) is a new avian reverse transcriptase that has been shown to be useful for high temperature cDNA synthesis to improve RT-PCR (Schwabe et al., 1998). It is cloned RT in which the active site of the RNase H domain has been mutated thereby reducing the RNase H by 99.5% as compared to native AMV. Thermoscript is operative in the temperature range between about 50° C. and about 70° C., a description of the efficacy of the Thermoscript™ at this temperature range is given in a FIG. 2 of the product description on the manufacturer' web site at http://www2.lifetech.com/catalog/techline/molecular_biology/product_description/thrmscrp.html. The optimized conditions for first strand synthesis by Therrnoscript™ have been described by Schwabe et al, 1998. Briefly, the 20 μl reaction mixture for the synthesis contains 50 mM Tris-acetate (pH 8.4); 75 mM K-acetate; 8 mM Mg-acetate; 5 mM dithioreitol; 1 mM each of dATP, DTTP, dCTP and dGTP; 0.5 μg oligo (dT); 2.5 mg RNA; 40 units RNase inhibitor and 15 units Thermoscript RT. The RT-PCR procedure, total cell RNA and oligo(dT) are incubated at 65° for 5 minutes and cooled on wet ice and cDNA synthesis reaction mixture is added. The reaction tubes are transferred to a prewarmed heating block and incubated for 50 minutes. Following RT inactivation, RNA is degraded by an RNase H. For PCR 20 μl cDNA reaction mixture is added to a 50 μl PCR mixture and incubated for 2 minutes at 94° C. PCR conditions involved 35 cycles of 94° C. for 30 s. 55–60° for 30 s. and 68–72° for 1 to 15 minutes. polymerases used for this method were Platinum Taq™ and eLONGase®.

rTth Reverse Transcriptase. The GeneAmp Thermostable rTth Reverse Transcriptase (Perkin-Elmer) catalyses the reverse transcription of RNA to cDNA at elevated temperature (60–70° C.) and subsequently amplifies cDNA using the same recombinant thermostable enzyme—rTth DNA Polymerase. The procedure begins with first strand cDNA synthesis from RNA, with rTth DNA Polymerase acting as a reverse transcriptase in the presence of $MnCl_2$ (Myers and Gelfand, 1991; Young et al, 1993). Subsequently, in the presence of $MgCl_2$, Chelating Buffer, and the second primer, synthesis of second strand cDNA and amplification of cDNA is initiated.

The ability of thermostable rTth DNA Polymerase to efficiently reverse transcribe RNA templates at 70° C. is useful in the present invention because the secondary structures are unstable at the higher reaction temperatures. An additional advantage of performing reverse transcription at higher temperatures is increased specificity of primer hybridization and subsequent extension by the rTth DNA Polymerase and therefore sensitivity of the reaction.

Reverse transcription using rTth DNA Polymerase is accomplished using a sincle specific oligonucleotide primer complementary to the 3'-terminus of the RNA. Subsequent PCR amplifications are achieved using specific oligonucleotide primer pairs at intervals progressively 3' to the resultant first-strand cDNA. The reverse transcription is performed at 60 ° C. for 2 hours, followed by a 1 minute predenaturation step at 95° C. then 40 cycles of 95° C. for 15 s, 65° C. for 30 s, for each primer pair. Starting template can be a poly(A) RNA or RNA from a civen tissue with a target copy number of approximately $10^8$ copies. The tissue RNA can be isolated from any desired tissues by techniques well known to those of skill in the art and also by techniques described elsewhere is the specification.

b. DNA polymerases

Havinge produce the first strand of the DNA species using reverse transcription, the present invention also contemplates the use of various DNA polymerases to produce the second strand of the double-stranded cDNA moiety. Exemplary polymerases are described below.

Bst DNA Polymerase, Large Fragment. Bst DNA Polymerase Large Fragment is the portion of the Bacillus setearohermophilus DNA Polymerase protein that contains the 5'→3' polymerase activity, but lacks the 5'→3' exonuclease domain. BST Polymerase Large Fragment is prepared from an *E. coli* strain containing a genetic fusion of the *Bacillus stearoihermophilus* DNA Polymerase gene, lacking the 5'→3' exonuclease domain, and the gene coding for *E. coli* maltose binding protein (MBP). The fusion protein is purified to near homogeneity and the MBP portion is cleaved off in vitro. The remaining polymerase is purified free of MBP (Iiyy et al., 1991).

Bst DNA polymerase can be used in DNA sequencing through high GC. regions (Hugh and Griffin, 1994; McClary et al., 1991) and Rapid Sequencing from nanogram amounts of DNA template (Mead et al., 1991). The reaction buffer is 1×ThermoPol Butter (20 mM Tris-HCl (pH 8.8 at 25° C.), 10 mM KCl, 10 mM $(NH_4)_2SO_4$, 2 mM $MgSO_4$, 0.1% Triton X-100). Supplied with enzyme as a 10×concentrated stock.

Bst DNA Polymerase does not exhibit 3'→5' exonuclease activity. 100 μl BSA or 0.1% Triton X-100 is required for long term storage. Reaction temperatures above 70° C. are not recommended. Heat inactivated by incubation at 80° C. for 10 min. Bst DNA Polymerase cannot be used for thermal cycle sequencing. Unit assay conditions are 50 mM KCl, 20 mM Tris-HCl (pH 8.8), 10 mM $MgCl_2$, 30 nM M13 mp18 ssDNA, 70 nM M13 sequencing primer (-47) 24 mer, 200 μM daTP, 200 μM dCTP, 200 μM dGTP, 100 μM $^3$H-dTTP, 100 μg/ml BSA and enzyme. Incubate at 65° C. Storage buffer is 50 mM KCl, 10 mM Tris-HCl (pH 7.5), 1 mM dithiothreitol, 0.1 mM EDTA, 0.1% Triton-X-100 and 50% glycerol. Storage is at –20° C.

$VENT_R$® DNA Polymerase and $VENT_R$® (exo⁻) DNA Polymerase. $Vent_R$ DNA Polymerase is a high-fidelity thermophilic DNA polymerase. The fidelity of $Vent_R$ DNA Polymerase is 5–15-fold higher than that observed for Taq DNA Polymerase (Mattila et al., 1991; Eckert and Kunkel, 1991). This high fidelity derives in part from an integral 3'→5' proofreading exonuclease activity in $Vent_R$ DNA Polymerase (Mattila el al., 1991; Kong et al., 1993). Greater than 90% of the polymerase activity remains following a 1 h incubation at 95° C.

$Vent_R$ (exo⁻) DNA Polymerase has been genetically engineered to eliminate the 3'→5' proofreading exonuclease activity associated with $Vent_R$ DNA Polymerase (Kong et al., 1993). This is the preferred form for high-temperature dideoxy sequencing reactions and for high yield primer extension reactions. The fidelity of polymerization by this form is reduced to a level about 2-fold higher than that of Taq DNA Polymerase (Mattila et al, 1991; Eckert and Kunkel, 1991). $Vent_R$ (exo⁻) DNA Polymerase is an excellent choice for DNA sequencing.

Both $Vent_R$ and $Vent_R$ (exo-) are purified from strains of *E. coli* that carry the Vent DNA Polymerase acne from the archaea *Thermococcus litoralis* (Perler et al., 1992). The native organism is capable of growth at up to 98° C. and was isolated from a submarine thermal vent (Belkin and Jannasch, 1985). They are useful in primer extension, thermal cycle sequencing and high temperature dideoxy-sequencing.

DEEP $VENT_R$™ DNA Polymierase and DEEP $VENT_R$™ (exo⁻) DNA Polymerase. Deep $Vent_R$ DNA Polymerase is the second high-fidelity thermophilic DNA polymerase available from New England Biolabs. The fidelity of Deep $Vent_R$ DNA Polymerase is derived in part from an integral 3'→5' proofreading exonuclease activity. Deep $Vent_R$ is even more stable than $Vent_R$ at temperatures of 95° C. to 100° C.

Deep $Vent_R$ (exo-) DNA Polymerase has been genetically engineered to eliminate the 3'→5' proofreading exonuclease activity associated with Deep $Vent_R$ DNA Polymerase. This exo- version can be used for DNA sequencing but requires different dNTP/ddNTP ratios than those used with $Vent_R$ (exo-) DNA Polymerase. Both Deep $Vent_R$ and Deep $Vent_R$ (exo-) are purified from a strain of *E. coli* that carries the Deep $Vent_R$ DNA Polymerase gene from *Pyrococcus species* GB-D (Perler et al., 1996). The native organism was isolated from a submarine thermal vent at 2010 meters (Jannasch et al., 1992) and is able to grow at temperatures as high as 104° C. Both enzymes can be used in primer extension, thermal cycle sequencing and high temperature dideoxy-sequencing.

T7 DNA Polymerase (unmodified). T7 DNA polymerase catalyzes the replication of T7 phage DNA during infection. The protein dimer has two catalytic activities: DNA polymerase activity and strong 3'→5' exonuclease (Hori et al., 1979; Engler et al., 1983; Nordstrom et al, 1981). The hich fidelity and rapid extension rate of the enzyme make it particularly useful in copying long stretches of DNA template.

T7 DNA Polymerase consists of two subunits: T7 gene 5 protein (84 kilodaltons) 5 and E. coli thioredoxin (12 kilodaltons) (Hori et al, 1979; Studier et al., 1990; Grippo and Richardson, 1971; Modrich and Richardson, 1975; Adler and Modrich, 1979). Each protein is cloned and overexpressed in a T7 expression system in E. coli (Studier et ah., 1990). It can be used in second strand synthesis in site-directed mutagenesis protocols (Bebenek and Kunkel, 1989).

The reaction buffer is 1×T7 DNA Poly,merase Buffer (20 mM Tris-HCl (pH 7.5), 10 mM $MgCl_2$, 1 mM dithiothreitol). Supplement with 0.05 mg/ml BSA and dNTPs. Incubate at 37° C. The high polymerization rate of the enzyme makes long incubations unnecessary. T7 DNA Polymerase is not suitable for DNA sequencing.

Unit assay conditions are 20 mM Tris-HCl (pH 7.5), 10 mM $MgCl_2$, 1 mM dithiothreitol, 0.05 mg/ml BSA, 0.15 mM each dNTP, 0.5 mM heat denatured calf thymus DNA and enzyme. Storage conditions are 50 mM $KPO_4$ (pH 7.0), 0.1 (M EDTA, 1 mM dithiothreitol and 50% glycerol. Store at −20° C.

DNA Polymerase I (E. coli). DNA Polymerase I is a DNA-dependent DNA polymerase with inherent 3'→5' and 5'→3 ' exonuclease activities (Lehman, 1981). The 5'→3' exonuclease activity removes nucleotides ahead of the arowing DNA chain, allowing, nick-translation. It is isolated from E. coli CM 5199, a lysogen carrying λpolA transducing phage (Murray and Kelley, 1979). The phage in this strain was derived from the original polA phage encoding wild-type Polymerase I.

Applications include nick translation of DNA to obtain probes with a high specific activity (Meinkoth and Wahl, 1987) and second strand synthesis of cDNA (Gubler and Hoffmann, 1983; D'Alessio and Gerard, 1988). The reaction buffer is E. coli Polymerase I/Klenow Buffer (10 mM Tris-HCl (pH 7.5), 5 mM $MgCl_2$, 7.5 mM dithiothreitol). Supplement with dNTPs.

DNase I is not included with this enzyme and must be added for nick translation reactions. Heat inactivation is for 20 min at 75° C. Unit assay conditions are 40 mM $KPO_4$ (pH 7.5), 6.6 mM $MgCl_2$, 1 mM 2-mercaptoethanol, 20 $\mu$M dAT copolymer, 33 $\mu$M dATP and 33 $\mu$M $^3$H-dTTP. Storage conditions are 0.1 M $KPO_4$ (pH 6.5), 1 mM dithiothreitol, and 50% glycerol. Store at −20° C.

DNA Polymerase I, Large (Klenow) Fragment. Klenow fragment is a proteolytic product of E. coli DNA Polymerase I which retains polymerization and 3'→5' exonuclease activity, but has lost 5'→3' exonuclease activity. Klenow retains the polymerization fidelity of the holoenzyme without degrading 5' termini.

A genetic fusion of the E. coli polA gene, that has its 5'→3' exonuclease domain genetically replaced by maltose binding protein (MBP). Klenow Fragment is cleaved from the fusion and purified away from MBP. The resulting Klenow fragment has the identical amino and carboxy termini as the conventionally prepared Klenow fragment.

Applications include DNA sequencing by the Sanger dideoxy method (Sanger et al., 1977), fill-in of 3' recessed ends (Sambrook et al., 1989), second-strand cDNA synthesis, random priming labeling tnd second strand synthesis in mutagenesis protocols (Gubler, 1987)

Reactions conditions are 1×E. Coli Polymerase I/Klenow Buffer (10 mM Tris-HCl (pH 7.5), 5 mM MgCl2, 7.5 mM dithiothreitol). Supplement with dNTPs. Klenow fragment is also 50% active in all four standard NEBuffers when supplemented with dNTPs. Hleat inactivated by incubating at 75° C. for 20 min. Fill-in conditions: DNA should be dissolved, at a concentration of 50 $\mu$/ml, in one of the four standard NEBuffers (1×) supplemented with 33 $\mu$M each dNTP. Add 1 unit Klenow per $\mu$g DNA and incubate 15 min at 25° C. Stop reaction by adding EDTA to 10 mM final concentration and heating at 75° C. for 10 min. Unit assay conditions 40 mM KPO4 (pH 7.5), 6.6 mM MgCl2, 1 mM 2-meraptoethanol , 20 $\mu$M dAT copolymer, 33) $\mu$M dATP and 33 $\mu$M $^3$H-dTTP. Storace conditions are 0.1 M $KPO_4$ (pH 6.5), 1 mM dithiothreitol, and 50% glycerol. Store at −20° C.

Klenow Fragment (3'→5' exo$^-$). Klenow Fragment (3'→5' exo$^-$) is a proteolytic product of DNA Polymerase I which retains polymerase activity, but has a mutation which abolishes the 3'→5' exonuclease activity and has lost the 5'→3' exonuclease (Derbyshire el al., 1988).

A genetic fusion of the E. coli polA gene, that has its 3'→5' exonuclease domain genetically altered and 5'→3' exonuclease domain replaced by maltose binding protein (MBP). Klenow Fragment exo- is cleaved from the fusion and purified away from MBP. Applications include random priming labeling, DNA sequence by Sanger dideoxy method (Sanger el al., 1977), second strand cDNA synthesis and second strand synthesis in mutagenesis protocols (Gubler, 1987).

Reaction buffer is 1×E. coli Polymerase I/Klenow Buffer (10 mM Tris-HCl (pH 7.5), 5 mM $MgCl_2$, 7.5 mM dithiothreitol). Supplement with dNTPs. Klenow Fragment exo- is also 50% active in all four standard NEBuffers when supplemented with dNTPs. Heat inactivated by incubating at 75° C. for 20 min. When using Klenow Fragment (3'→5' exo-) for sequencing DNA using the dideoxy method of Sanger et al. (1977), an enzyme concentration of 1 unit/5 $\mu$l is recommended.

Unit assay conditions are 40 mM KPO4 (pH 7.5), 6.6 mM $MgCl_2$, 1 mM 2-mercaptoethanol, 20 $\mu$M dAT copolymer, 33 $\mu$M dATP and 33 $\mu$M $^3$H-dTTP. Storage conditions are 0.1 M $KPO_4$ (pH 7.5), 1 mM dithiothreitol, and 50% glycerol. Store at −20° C.

T4 DNA Polymerase. T4 DNA Polymerase catalyzes the synthesis of DNA in the 5'→3' direction and requires the pres ence of template and primer. This enzyme has a 3'→5' exonuclease activity which is much more active than that found in DNA Polymerase I. Unlike E. coli DNA Polymerase I, T4 DNA Polymerase does not have a 5'→3' exonuclease function.

Purified from a strain of E. coli that carries a T4 DNA Polymerase overproducing plasmid. Applications include removing 3' overhangs to form blunt ends (Tabor and Struhl, 1989; Sambrook et al., 1989), 5' overhang fill-in to form blunt ends (Tabor and Struhl, 1989; Sambrook et al., 1989), single strand deletion subdloning (Dale et al, 1985), second strand synthesis in site-directed mutagenesis (Kunkel et al., 1987), and probe labeling using replacement synthesis (Tabor and Struhl, 1989; Sambrook et al., 1989).

The reaction buffer is 1×T4 DNA Polymerase Buffer (50 mM NaCl, 10 mM Tris-HCl, 10 mM $MgCl_2$, 1 mM dithiothreitol (pH 7.9 at 25° C.)). Supplement with 40 $\mu$g/ml BSA and dNTPs (not included in supplied 10×buffer). Incubate at temperature suggested for specific protocol.

It is recommended to use 100 μM of each dNTP, 1–3 units polymerase/μg DNA and incubation at 12° C. for 20 min in the above reaction buffer (Tabor and Struhl, 1989; Sambrook et al., 1989). Heat inactivated by incubating at 75° C. for 10 min. T4 DNA Polymerase is active in all four standard NEBuffers when supplemented with dNTPs.

Unit assay conditions are 50 mM NaCl, 10 mM Tris-HCl, 10 mM $MgCl_2$, 1 mM dithiothreitol (pH 7.9 at 25° C.), 33 μM dATP, dCTP and dGTP, 33 μM $^3$H dTTP, 70 μg/ml denatured calf thymus DNA, and 170 μg/ml BSA. Note: These are not suggested reaction conditions; refer to Reaction Buffer. Storage conditions are 100 mM $KPO_4$ (pH 6.5), 10 mM 2-mercaptoethanol and 50% glycerol. Store at −20° C.

Taq Polymerases. Native Taq™ (Perkin-Elmer) DNA Polymerase is a thermostable, 94-kDa DNA polymerase isolated from *Thermus aquaticus* YT1. It is primarily used for exact replication of studies performed prior to the availability of recombinant AmpliTaq DNA Polymerase. AmpliTaq DNA Polymerase is a 94-kDa, gelatin-free, thermostable, recombinant DNA polymerase obtained by expression of a modified form of the Taq DNA Polymerase gene cloned in *E. coli* (Lawyer el al., 1989; Lawyer et al., 1993).

The thermal activity profile of AmpliTaq DNA Polymerase is ideal for PCR applications because its optimal activity is in the same range at which stringent annealing of primers occurs (55° C.–75° C.). The enzyme's PCR cycling half-life is 50 cycles at 95° C., providing sufficient thermostability such that there is no substantial loss of enzymatic activity, even after repeated exposure to the highest temperatures recommended in most PCR protocols. The enzyme has a 5'→3' exonuclease activity which has been exploited in development of a homogeneous simultaneous signal generation assay (Holland et al., 1991) and it lacks 3'→5' exonuclease activity.

Tfl DNA Polymerase. Tfl is yet another polymerase enzyme with an apparent molecular weight of approximately 94kDa. It was isolated from *Thermus flavus* (Kaledin el al., 1981). The isolated enzyme is thermostable and has a temperature optimum on the DNA templates at 70° degrees and that on RNA templates at 50 degrees. The enzyme does not appear to contain contaminant endo- and exonuclease activities. For maximal activity, the enzyme requires the presence of template, four deoxyribonucleoside triphosphates and monovalent and bivalent cations in the incubation mixture. The enzyme is highly active when "activated" DNA, poly(dA)-poly(dT), poly(dA)-oligo(dT) 10 and poly (rA)-oligo(dT) 10 are used as templates, moderately active on single-stranded and double-stranded DNAs and inactive on poly(rC)-oligo(dG)12–18 and native RNA molecules. Tfl is commercially available from a variety of sources including Promega.

Tht DNA Polymerase was isolated from *Thermus thermophilus* HB-8 (Ruttimann et al., 1985). This enzyme catalyzes the DNA polymerization, of nucleotides into duplex DNA in the 5'→3' direction in the presence of $MgCl_2$. Also the enzyme catalyzes RNA polymerization in the presence of $MgCl_2$. The ability of Tth DNA polymerase to act as an RT at elevated temperatures is particularly useful in the context of the present invention.

Tli DNA polymerase. Tli DNA polymerase is an extremely thermostable polymerase that replicates DNA at 75° C. and remains functional even after incubation at 100° C. Tli DNA polymerase has an integral 3'→5→ exonuclease activity (proofreading) function. The enzyme has a molecular weight of approximately 90 kDa (Mattila et al., 1991) and is commercially available from a variety of sources.

UlTma™ DNA Polymerase is a thermostable DNA polymerase specifically designed, thoroughly optimized and tested for its ability to repair 3' -mismatches in PCR amplification, to provide high yield of specific PCR product, and to produce blunt-ended PCR products suitable for cloning and gene expression. UlTma DNA Polymerase, a 70-kDa recombinant enzyme, is encoded by a modified form of a *Thermotoga maritima* DNA polymerase gene which has been cloned and expressed in *E. coli* (U.S. Pat. No. 5,310, 652, incorporated herein by reference). The enzyme has been specifically engineered to achieve an optimal balance between polymerase and proofreading activity. It has also been optimized for higher yield by using a hot start reaction.

C. Colorectal Cancer-A study in cDNA Library Generation

A particular goal of the present invention is to provide methods for preparing cDNA libraries from mRNAs derived from tumors and their corresponding normal tissue. As an example, the present invention focuses on tumors of the colon, however, it is understood that using the techniques of the present invention libraries may be constructed for any tumor. Colorectal cancer (CRC) can be classified into three major types on the basis of family history and clinical features: sporadic (without familial history), adenomatous polyposis (APC), and hereditary nonpolyposis colon cancer (HNPCC). APC. includes both familial adenomatous polyposis and Gardner's syndrome and is inherited in an autosomal dominant fashion.

CRC arises as a result of a series of genetic alterations that are paralleled by progression of the normal colonic mucosa through the various histologically identifiable stages of carcinogenesis (Fearon and Vogelstein, 1990). In the progression from adenoma to carcinoma, it appears that the order of the genetic events is not as important as the number of alterations that have accumulated. However, certain types of events tend to occur earlier, and others are more likely to occur later.

Molecular studies of CRC. have been facilitated by the ease with which one can obtain tissue at the various stages of colon carcinogenesis. The earliest histological transition is from normal mucosa to hyperplasia. Early adenomas can then arise from these areas of hyperproliferation and are likely to be classified histologically as tubular adenomas. These adenomas progress into intermediate adenomas that are likely to have developed a villous component and are thus classified as tubulovillous. As an adenoma progresses to a late adenoma, it is likely to be composed predominantly of villous elements with severe dysplasia, and carcinoma in situ usually arises from this villous component of the adenoma. Eventually, if not removed, malignant cells erode through the basement membrane, then through the stalk of the polyp and then invade the colorectal lymphatics and nerves as well as breaking through the serosa into the peritoneal cavity or perirectal tissues.

a. Hereditary CRC

Adenomatous polyposis coli (APC) accounts for approximately 1% of the colorectal cancer in the Western world (Mulvihill, 1983; Jarvinen, 1992) and includes both familial adenomatous polyposis (FAP) and Gardner's syndrome (GS). Gardner's syndrome is similar to FAP except that GS patients also have benign extracolonic tumors such as osteomas, epidermoid cysts, desmoid tumors, and dental abnormalities. APC occurs as a result of germline mutations in the APC gene.

Most hereditary nonpolyposis colorectal cancer (HNCPP) is due to germline mutations in DNA mismatch repair (MMR) genes, which include hMSH2, hMLH1, hPMS1, hPMS2, and GTBP (Fishel el al., 1993; Leach et al., 1993;

Papadopoulos et al., 1994; Bronner et al., 1994; Papadopoulos et al., 1995). HNPCC is inherited in an autosomal dominant fashion and is estimated to account for 4–13% of all cases of colorectal carcinoma (Lynch et al., 1988). The cells of HNPCC carriers are thought to be MMR proficient as they have one mutant allele and one normal allele for one of the MMR genes. During tumor development, the normal allele is lost or mutated (Liu et al., 1995). The cells then become MMR deficient and subsequently begin to accumulate mutations, some of which contribute to the process of tumorigenesis.

One way to detect MMR deficiencies is by examining microsatellites, which are short tandem repeats of DNA that are distributed throughout the genome and tend to accumulate replication errors (RERs) at a much higher rate than other sequences in the genome (Hearne el al., 1992; Weber, 1990; Thibnodeau et al., 1993). RER can be detected in tumors from HNPCC patients and a subset of sporadic CRCs by examining microsatellite repeat fragments, as the number of repeats in some of the microsatellites changes because of the defective repair pathway.

There are some differences in the progression of the two major types of hereditary CRC. For example, although all forms of CRC are thought to arise from adenomas, the rate of conversion from adenoma to carcinoma varies between the two types. In HNPCC the incidence of adenomas is not particularly high, but the rate of conversion of adenoma to carcinoma appears to be significantly faster than in APC or sporadic CRC (Lynch et al., 1993; Jasse and Stewart, 1992). In contrast, patients with APC mutations have a dramatically increased rate of adenoma formation, but the rate of conversion of adenoma to carcinoma is relatively low (Bussey, 1990).

b. Sporadic CRC

The earliest events in sporadic CRC have not been elucidated. A subset of sporadic CRC (~15–25%) display RER. The pathways of tumorigenesis in these tumors would be expected to be similar to those of patients with germline mutations in mismatch repair genes, with many of the targets of mutation being genes containing simple repeated sequences. Target of RER within gene coding regions include the genes for the transforming growth factor-beta type II receptor (Markowitz et al., 1995), the insulin-like growth factor II receptor (Souza et al., 1996), BAX (Rampino et al., 1997), and β2-microglobulin (Bicknell et al., 1996).

Aneuploidy is a second mechanism by which CRC tumors may display genome instability and results from a defect in chromosome segregation (Lengauer et al., 1997). CRCs with microsatellite instability do not tend to display aneuploidy. In a study comparing HNPCC tumor specimens to sporadic carcinomas, it was determined that 65% of the HNPCC tumors were diploid as opposed to only 40% of the sporadic carcinomas. Aneuploidy is a relatively early event in APC, and therefore the pathways of tumorigenesis for APC and sporadic CRC are frequently similar (Quirke et al., 1986).

Because a similar percentage (60%) of sporadic adenomas and sporadic carcinomas were found to contain APC gene mutations, it is thought that APC gene mutations play a role in the development of the major proportion of sporadic CRC early in colorectal carcinogenesis (Powell et al, 1992). Pathways of tumorigenesis in these tumors would be expected to be similar to those for patients with hereditary APC.

c. Library Preparation

In certain instances, preparing cDNA libraries from a desired tissue will require isolating mRNA from a tumor or other cell sample. In such an isolation procedure the cells are lysed in the presence of a safe, non-toxic Ribonuclease (RNase)/Protein degrader solution and SDS. The lysate then is incubated with oligo (dT) cellulose which allows interaction of the poly(A) tail at the 3'-end of most eukaryotic mRNAs. Non-bound material is washed away and purified mRNA is eluted into a mini-column via microcentrifugation. There are many commercially available kits that ensure that handling is minimal. Such kit come complete with lysis solutions and buffers, oligo (dT) cellulose supply, spin columns and microcentrifugation tubes. The quality and purity of mRNA samples can be checked on agarose gels.

The cDNA library is generated with SaverTimer cDNA synthesis kit (Pharmacia, Piscataway, N.J.) following the manufacturer's protocol. Set 1 consisted of A-, G-, and C-anchored oligo-dT primers. Set 2 consisted of A-, G-, AC-, GC-, and CC-anchored primers. Double-stranded cDNA was cloned into pBS KS(−) vector. Positive clone identification and sequencing analysis were the same as above.

Once the cDNA libraries have been synthesized as described herein, it will be advantageous to determine if the length of cDNAs in the resulting libraries are representational. A number of criteria will be used to judge the representation of libraries. An initial consideration is that oligo dT will be used as the primer for first strand synthesis and that virtually all mRNAs have a 3' poly (A) tail. Another factor is clearly the size of the library that is prepared from a given cell line or tissue. The upper range of distinct mRNAs expressed in any given tissue is approximately 20,000.

Using the following formula one can determine the size of a library that is required to insure virtually complete representation: $p=1-(1-f)^n$, where p is the probability of representation, f is the frequency of occurrence of a given mRNA, and n is the number of clones in the library. Taking an extreme case and calculating p for a low abundant mRNA species that occurs at a frequency of one in one million (50 times lower than the average), an that a library of one million clones will contain this species at a probability of 0.63 and a library of 10 million clones will contain this species at a probability of 0.99995. Libraries that the inventor has made in the past typically contain over 20 million clones indicating that, barring a species-specific elimination of a particular clone, virtually all species should be represented in libraries of this size.

Two other methods will be usedl to insure representation as described below. The beta-actin gene is a ubiquitously expressed gene that is typically represented in a library at a frequency of 0.1% (Leader et al., 1986), and thus can be used as a marker to determine if it is occurring at the expected frequency in a given library. Screening of a small portion of the library can be performed to insure that this gene is represented at the approximately 0.1% frequency.

A second method that will be employed is to use a collection of currently available DNA repair genes to determine if they are all represented in a library. These genes are: ERCC1, XPA, XPB, XPC, XPD, XPF, XPG, CSA, CSB, HHR23B. All of these genes are ubiquitously expressed, all are relatively low abundant mRNA species, and cover a range of sizes from 1 kb to about 6 kb. PCR primers for each of these genes are prepared and used to determine that they are represented in the created libraries in the appropriate fractions. These genes will be used in addition to the specific genes described herein. Finally, in some cases particular cDNAs may be lost by rearrangement during passage in *E. coli*. To reduce this possibility, a RecA strain of *E. coli*, DH10B, will be used which also has a very high frequency of electroporation.

D. Primers and probes

The present invention will employ various primers and probes for initiating the synthesis of long cDNA moieties form a given mRNA. Also, PCR primers may be designed for specific penes and are used to determine whether the particular genes is represented in the libraries created in the present invention.

a. Primer Design

The term primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In certain aspects of the present invention, oligo-dT primers will be used in reverse transcription and amplification reactions. These primers are 3'-anchored, i.e., contain particular bases at their 3' ends. These bases are the singlets A and G or the doublets, CC, CG or CA. This creates a set of five primers which give the highest possible coverage in random priming reactions (91.72%) without sacrifice of fidelity.

The particular length of the primer is not believed to be critical, with the dT sequence ranging from about 10 to about 25 bases, with 11 being a preferred embodiment. In some embodiments, the primers are labeled with radioactive species ($^{32}$P, $^{14}$C, $^{35}$S, $^{3}$H, or other isotope), with a fluorophore (rhodamine, fluorescein, GFP) or a chemiluminescent label (luciferase).

Another type of primer, according to the present invention, is a arbitrary or random primer. Typically, such primers are used in combination with the anchored primer in a PCR-type reaction. The arbitrary primer serves to prime synthesis on the opposite strand as the anchored dT primer, permitting amplification. Such random primers are well known in the art and commercially available.

b. Probes

In various contexts, it may be usefull to use oligo or polynucleotides as probes for complementary or hybridizing DNA or RNA molecules. In this regard, one may include particular "target" sequences in the oligo's of the present invention in order to detect the products by probe hybridization. Alternatively, the probes may recognize unique sequences in the amplified regions upstream of the oligo-dT primers.

c. Hybridization

Suitable hybridization conditions will be well known to those of skill in the art. Typically, the present invention relies on high stringency conditions (low salt, high temperature), which are well known in the art. Conditions may be rendered less stringent by increasing salt concentration and decreasing temperature. For example, a medium stringency condition could be provided by a bout 0.1 to 0.25 M NaCl at temperatures of about 37° C. to about 55° C., while a low stringency condition could be provided by about 0.15 M to about 0.9 M salt, at temperatures ranging, from about 20° C. to about 55° C. Thus, hybridization conditions can be readily manipulated, and thus will generally be a method of choice depending on the desired results.

d. Primer Synthesis

Oligonucleotide synthesis is performed according to standard methods. See, for example, Itakura and Riggs (1980). Additionally, U.S. Pat. No. 4,704,362; U.S. Pat. No. 5,221, 619 U.S. Pat. No. 5,583,013 each describe various methods of preparing synthetic structural genes.

Oligontcleotide synthesis is well known to those of skill in the art. Various different mechanisms of owlionucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244 each of which is incorporated herein by reference.

Basically, chemical synthesis can be achieved by the diester method, the triester method polynucleotides phosphorylase method and by solid-phase chemistry. These methods are discussed in further detail below.

Diester method. The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligodeoxynucleotides (Gillam et al., 1978; Gillam et al., 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage, and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

E. Amplification Methods

The present invention contemplates the use of amplification methods. A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. if the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

Another method for amplification is the ligase chain reaction ("LCR"), disclosed in EP No. 320 308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Followino polymerization, DNA/RNA hybrids are digested with RNase H while double-stranded DNA molecules are heat denatured again. In either case the single stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double-stranded DNA, and then transcribed once again with an RNA polymerase such as T7 or SP6. The resulting products, whether truncated or complete, indicate target specific sequences.

Davey et al., EP No. 329 822 disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an PNase specific for RNA in duplex with either DNA or RNA). The resultant ssDNA is a template for a second primer, which also includes the sequences of an RNA polymerase promoter (exemplified by T7 RNA polymerase) 5' to its homology to the templates This primer is then extended by DNA polymerase (exemplified by the large "Klenow" fragment of *E. coli* DNA polymerase I), resulting in a double-stranded DNA ("dsDNA") molecule, havingt a sequence identical to that of the original RNA be tween the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of eith er DNA or RNA.

Miller et al., PCT Application WO 89/06700 disclose a nucleic acid sequence amplification scheme based on the hybridization of a promoter/primer sequence to a target single-strand ed DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989).

Methods based on ligation of two (or more) oligonucleotides in the presence of nucleic acid having the sequence of the resulting "di-oigonucleotide", thereby amplifying the di-oligionucleotide, may also be used in the amplification step of the present invention. Wu et al. (1989).

F. Differential Display

RNA fingerprinting is a means by which RNAs isolated from many different tissues, cell types or treatment aroups may be sampled simultaneously to identify RNAs whose relative abundance s vary. Two forms of this technology were developed simultaneously and reported in 1992 as RNA fingerprinting by differential display (Liang and Pardee, 1992; Welsh et al., 1992). (See a lso Liang and Pardee, U.S. Pat. No. 5,262,311, incorporated herein by reference in its entirety.) Both tech niques were utilized in the studies described below . Some of the studies describ ed herein were performed similarly to Donahue et al., 1994.

All forms of RNA fingerprinting by PCR are theoretically similar but differ in their primer design and application. The most striking difference between differential display and other methods of RNA fingerprinting is that differential display utilizes anchoring primers that hybridize to the polyA tails of mRNAs. As a consequence, the PCR products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo-dT. The oligo-dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from different cell derived RNAs using. the same oligonucleotide primers identifies mRNAs that are differentially expressed.

RNA fingerprinting technology has been demonstrated as being effective in identifying genes that are differentially expres sed in cancer (Liang and Pardee, 1992; Sager et al., 1993 ; Mok et al., 1994; Watson et al., 1994; Chen et al., 1995; An et al., 1995). The present invention utilizes the RNA fingerprinting, technique to identify genes that are differentially expressed in colorectal cancer and create cDNA libraries from such cancers. These studies utilized RNiks isolated from tumor tissues and tumor-derived cell lines that behave as tumors cells with different metastatic potential.

The underlying concept of these studies was that genes that are differentially expressed in cells with different metastatic potentials may be used as indicators of metastatic potential. Since metastasis is a prerequisite for prostate cancer progression to life threatening pathologies, indicators of metastatic potential are likely to be indicators of pathological potential.

Cells often are harvested in late log phase of growth. RNA may be isolated by the guanidinium thiocyanate method (Chomczynski and Sacchi, 1987). After RNA isolation, the nucleic acids are precipitated with ethanol. The precipitates are pelleted by centrifugation and redissolved in water. The redissolved nucleic acids are then digested with RNase-free DNase I (Boehringer Mannheim, Inc.) following the manufacturer's instructions, followed by organic extraction with phenol:chloroform:isoamyl alcohol (25:24:1) and reprecipitation with ethanol.

The DNase I treated RNA is then pelleted by centrifugation and redissolved in water. The purity and concentration of the RNA in solution is estimated by determining optical density at wave lengths of 260 mn and 280 nm (Sambrook et al., 1989). A small aliquot of the RNA is separated by gel electrophoresis in a 3% formaldehyde gel with MOPS buffer (Sambrook et al., 1989) to confirm the estimation of concentration and to determine if the ribosomal RNAs were intact. This RNA is referred to as total cell RNA.

There were two kinds of RNA fingerprinting studies performed with the total cell RNA. The first of these kinds of studies follow the differential display protocol of Liang and Pardee (1992) except that they are modified by using 5' biotinylated primers for nonisotopic PCR product detection.

In these studies, 0.2 $\mu$g of total cell RNA are primed for reverse transcription with an anchoring primer according to the present invention, then two arbitrarily chosen nucleotides, including all of the possible combinations of each nucleotide at these positions. Reverse transcription is performed with 200 units of MMLV (Moloney Murine Leukemia Virus) reverse transcriptase (GIBCO/BRL) in the presence of 50 mM Tris-HCl (pH 8.3), 75 mM KCl, 3 mM MgCl$_2$, 10 mM DTT, 500 $\mu$M dNTP, 1 $\mu$M anchored primer and 1 U/$\mu$l RNase inhibitor. The reaction mixture is incubated at room temperature for 10 minutes, then at 37° C. for 50 minutes. After reverse transcription the enzyme is denatured by heating to 65° C. for 10 minutes.

One tenth of the resulting reverse transcription reactions is then amplified by PCR using the same anchoring primer as used in the reverse transcription step and a second oligonucleotide of arbitrarily chosen sequences. The PCR reaction contains 10 mM Tris-HCl (pH 8.3), 50 mM KCl, 20 $\mu$M dNTP, 1.5 $\mu$M MgCl$_2$, 200 nM arbitrary decamer, 1 $\mu$M anchored primer, and 1 unit of Taq DNA polymerase (Boehringer Mannheim) in a 40 $\mu$l volume. The amplification is performed in a thermal cycler (MJ Research) for 30 cycles with denaturing at 94° C. for 30 sec, annealing at 40° C. for 2 min, and extending at 72° C. for 30 sec.

The PCR products are then separated on a 6% TBE-urea sequencing gel (Sambrook et al., 1989) and detected by chemiluminescent reaction using the Seq-Light™ detection system (Tropix, Inc). Differentially appearing PCR products may be excised from the gels, reamplified using the same primers used in the original amplification, and cloned using the TA cloning strategy (Invitrogen, Inc. and Promega, Inc.).

The second type of RNA fingerprinting studies more closely resembled the protocol of Welsh et al. (1992). This approach uses a variation of the above as modified by the use of agarose gels and non-isotopic detection of bands by ethidium bromide staining (An et al., 1995). Total RNAs are isolated from the frozen prostate tissues or cultured cells as described (Chomczynski and Sacchi, 1987). Ten micrograms of total cellular RNAs are treated with 5 units of RNase-free DNAse I (GIBCO/BRL) in 20 mM Tris-HCl (pH 8.4), 50 mM KCl, 2 mM MgCl$_2$, and 20 units of RNase inhibitor (Boehringer Mannheim). After extraction with phenol/chloroform and ethanol precipitation, the RNAs are redissolved in DEPC-treated water.

Two $\mu$g of each total cell RNA sample are reverse transcribed into cDNA using randomly selected hexamer primers and MMLV reverse transcriptase (GIBCO/BRL). PCR was performed using one or two arbitrarily chosen oligonucleotide primers (10-12-mers). PCR conditions are: 10 mM Tris-HCl (pH 8.3), 50 mM KCl, 1.5 mM MgCl$_2$, 50 $\mu$M dNTPs, 0.2 $\mu$M of primer(s), 1 unit of Taq DNA polymerase (GIBCO/BRL) in a final volume of 20 μl. The amplification parameters include 35 cycles of reaction with 30 sec denaturing at 94° C., 90 sec annealing at 40° C., and 60 sec extension at 72° C. A final extension at 72° C. is performed for 15 min. The resulting PCR products are resolved into a fingerprint by size separation by electrophoresis through 2% agarose gels in TBE buffer (Sambrook et al., 1989). The fingerprints are visualized by staining with ethidium bromide. No reamplification is performed.

Differentially appearing PCR products, that might represent differentially expressed genes, are excised from the gel with a razor blade, purified from the agarose using the Geneclean kit (Bio 101, Inc.), eluted in water and cloned directly into plasmid vectors using the TA cloning strategy (Invitrogen, Inc., and Promega, Inc.). These products are not reamplified after the initial PCR fingerprinting protocol.

G. Blotting Methods

In certain embodiments, blotting techniques will be used to examine the size of cDNAs made or to verify the completion of a PCR reaction. Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will bind a portion of the target sequence under renaturing conditions. Unbound probe is then removed, and detection is accomplished as described above.

H. Separation Methods

It normally is desirable, at one stage or another, to separate the amplification products from reagents, such as the template or excess primers, or from other amplification products. In one embodiment, amplification products are separated by agarose, agarose-acrylamide or polyacrylamide gel electrophoresis using standard methods. See Sambrook et al., 1989. When working with nucleic acids, denaturing PAGE is preferred.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

I. Expression Vectors

Within certain embodiments, the cDNA species generated herein are inserted into expression vectors to express various polynucleotides or provide libraries of cDNA in accordance with the present invention. Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

a. Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

b. Selectable Markers

In certain embodiments of the invention, the cells contain nucleic acid constructs of the present invention, a cell may be identified in vitro or in vivo by includin(g a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

J. Kits

All the essential materials and reagents required for performing Differential Display, creating cDNA libraries and performing RT-PCR may be assembled together in a kit. Such kits generally will comprise preselected primers and may include other oligo-and polynucleotides, such as probes and expression vectors. Also included may be enzymes suitable for amplifying nucleic acids including various polymerases (reverse transcriptases, Taq, Sequenase™, etc.), dNTPs and buffers to provide the necessary reaction mixture for amplification. Such kits also generally will comprise, in suitable means, distinct containers for each individual primer, probe, vector, dNTPs, buffer and enzyme(s).

K. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Methods

1. First Strand cDNA Synthesis

The following recipe is used for the synthesis of first strand cDNA from poly(A)+ RNA. Six to ten lag of poly (A)+ RNA are resuspended in 60 $\mu$l of DEPC treated H2O, boiled for 30 sec and placed on ice. Then add 20 $\mu$l 5×superscript buffer; 2 $\mu$l oligo-dT primer (1 $\mu$g/$\mu$l); 5 $\mu$l dNTPs (10 mM each); 0.5 $\mu$l [32P]$\alpha$ dCTP (optional); 5 $\mu$l RNase inhibitor (40 u/$\mu$l) and 8 $\mu$l Superscript™ RT (25 u/$\mu$l).

This retain mixture is incubated for 45 min at 45° C. After this incubation step, 10 $\mu$l MnCl$_2$ (10 mM) and 5 $\mu$l Retrotherm™ RT are added. This second reaction mixture is incubated for 15 min. at 74° C. This step is followed by the addition of 5 $\mu$l Superscript RT and incubate at 45° C. for 45 min. This is followed by a further incubation of at 74° C. The above conditions at 45° C. and 74° C. are repeated at least one more time. Because Retrotherm™ is a thermostable enzyme, it is not necessary to provide additional enzyme, however, additional enzyme may be added.

The reaction is quenched by adding 4.5 $\mu$l 0.25 M EDTA. 1 $\mu$l of the reaction mixture at each stage is removed to determine total and TCA precipitable counts. The amount of first strand synthesis is calculated with the following equation: TCA counts/total counts×66 $\mu$g first strand synthesized. Specific activity of product=10$^9$×TCA counts/$\mu$g first strand synthesized.

The synthesized first strand is isolated by adding 0.5 $\mu$l 10% SDS and extracting with phenol-chloroform and precipitation with 95% ethanol-2% potassium acetate. The resultant precipitate is washed with 70% ethanol.

2. Second Strand Synthesis

The pellet from first strand synthesis is resuspended by vigorous vortexing in 152 $\mu$l DEPC-treated H2O and 20 $\mu$l of 10 ×second strand buffer. To this suspension is added:

8 $\mu$l dNTPs (10 mM each)
  8 $\mu$l RNase H (1u/$\mu$l)
  DNA Pol. I (5 u/$\mu$l)

This reaction mixture is incubated at 15° C. for 1 hour followed by an incubation at room temperature for another hour. The double stranded cDNA is extracted and precipitated as above except that SDS is not used.

3. Addition of Linkers

In order to add linkers to the double stranded cDNA, the pellet from second strand synthesis is resuspended in 34.5 $\mu$l H2O and 4 $\mu$l 10 ×ligase buffer and 4$\mu$l spermidine (10 mM), 11.5 $\mu$l kinased oligo 1 (0.33 $\mu$g/$\mu$l), 15 $\mu$l kinased oligo 2 (0.33 $\mu$g/$\mu$l), 1 $\mu$l T4 DNA ligase (8 $\mu$/$\mu$l). The reaction mixture is incubated overnight at 15° C. The ligated double stranded cDNA is extracted and precipitated as described above. The pellet is then resuspended in 100 $\mu$l TE buffer.

4. Agarose Gel Fractionation of cDNA

For size fractionating the cDNA species generated, a 10×10 cm gel is used having a well that is 5-cm in width is obtained. The cDNA should be heated for 10 min at 65° C. to dissolve aggregates immediately prior to gel loading. The gel is run in TAE buffer for 3 hrs at 50 V. The 1 Kb ladder from BRL-Gibco or equivalent is used as a marker. A long-wave UV transilluminator or light should be used to observe the marker. Typically the cDNA is separated into four fractions: (1)>10 Kb; (2) 4–10 Kb; (3) 2–4 Kb; (4) 1–2 Kb, (5) 0.5–1 Kb. This step can, of course, be modified as desired.

The cDNA is recovered from the gel by the phenol freeze-fracture method (Bewsey et al., 1991). The agarose wedge is placed in a microcentrifuge tube with and equal volume of phenol and vortexed vigorously. The microcentrifuge tube is placed at −70° C. until frozen and then thawed at 37° C. A second, equal volume of phenol is added, the sample is subjected to vortexing, refrozen at −70° C. and thawed at 37° C. 50 µl deionized H2O is added, the sample is vortexed and centrifuged for 20 min at 14,000 rpm in a microcentrifuge. The supernatant is collected and extracted once each with phenol, phenol/chloroform (1:1), and chloroform. The cDNA is then precipitated by the addition of 1/10 volume of 3 M sodium acetate (pH 5.5) and 2.5 volumes of 95% ethanol. The recovered pellet is then washed in 70% ethanol. After resuspension in TE buffer, a small portion of each fraction is counted to determine the CPM recovered. The CPM is divided by the specific activity calculated above to obtain the mass of each fraction.

5. Ligation of cDNA to Vector and Electroporation

The volume of the ligation reaction will depend upon the amount of recovered cDNA but will typically range from 200 to 500 µl. Fraction 1 and 2: vector:cDNA ratio should be 1:2. The total concentration of DNA should be approximately 0.5 µg/ml. Fractions 3–5: vector:cDNA ratio should be 1:1. The total concentration of DNA should be approximately 1 µg/ml. Ligase concentration should be 4–8 u/100 µl. After ligation (usually overnight), the sample is extracted and precipitated as above and resuspended at a concentration of approximately 100–150 ng per 5 µl (but not less than 10 µl total) for electroporation.

Electroporation is performed with a Bio-Rad Gene Pulser in a 0.2 cm cuvette at settings of 25 µF, 200 Ω, and 2.5 kvolts. After electroporation an appropriate dilution of the cells is plated to determine the titer for each fraction. The method described above typically yields titers of 1–10×10$^7$ µg of vector with the average being 3–5×10$^7$. This efficiency requires very good electro-competent cells (5–10×109 µg pBR322). If DNA is to be prepared, the remainder of the sample is added to 1 liter LB medium plus 50 µg/ml ampicillin. After overnight culture small aliquots can be frozen in 15% glycerol for long term storage and the remainder can be used for DNA preparation. Starting with 8–10 µg of poly(A)+RNA, libraries that contain over 20 million total clones are readily obtained.

EXAMPLE 2

Dual RT Cycling Procedure for Preparing Long cDNAs.

The ATM transcript was subsequently shown to be approximately 12 kb in length (Savitsky et al., 1995a), although the coding region is approximately 9 kb in length (Savitsky et al., 1995b). In an attempt to prepare libraries that contained very long cDNAs and were thus more representational, a procedure was developed in which both a low temperature and a high temperature RT are used. The present invention is directed to this procedure for synthesizing long cDNAs.

Poly (A)+ RNA was prepared from HeLa cells as described (Glison el al., 1974; Ullrich et al., 1977). Five µg of RNA is boiled for 30 sec and then incubated with Superscript II reverse transcriptase at 45° C. for 45 min. in the buffer supplied by the manufacturer (Gibco-BRL) and with oligo-dT as a primer. Literature supplied by the manufacturer indicated that the enzyme performed first strand synthesis equally well if not better at 45° C. than at 37° C. In the next step, MnCl$_2$ is added to 0.75 mM (necessary for the Retrotherm enzyme) along with Retrotherm enzyme and the reaction is incubated at 74° C. for 15 min. A fresh aliquot of the Superscript enzyme is added and the sample incubated at 45° C. followed by another incubation at 74° C.

This protocol is repeated one more time for three cycles of incubation with both enzymes. This entire procedure can be conveniently performed in a temperature cycler with interruptions to add the Superscript enzyme. The procedure is simple and robust and should easily transfer to other laboratories with minimal effort.

The idea behind this protocol is that secondary structure present in the mRNA may block the progress of the Superscript RT at 45° C., while at 74° C. the secondary structure may be relieved, thus allowing the Retrotherm enzyme to pass through this region. Because of the low processivity of the Retrotherm enzyme additional cycles of incubation are performed with the Superscript enzyme again followed by incubation at 74° C. to complete the cDNA synthesis. In addition to the presence of secondary structure in the mRNA, there may exist natural pause sites for the RTs. The use of two different enzymes which may respond differently to these sites could reduce the inhibition of synthesis caused by these regions.

Figure 1B:
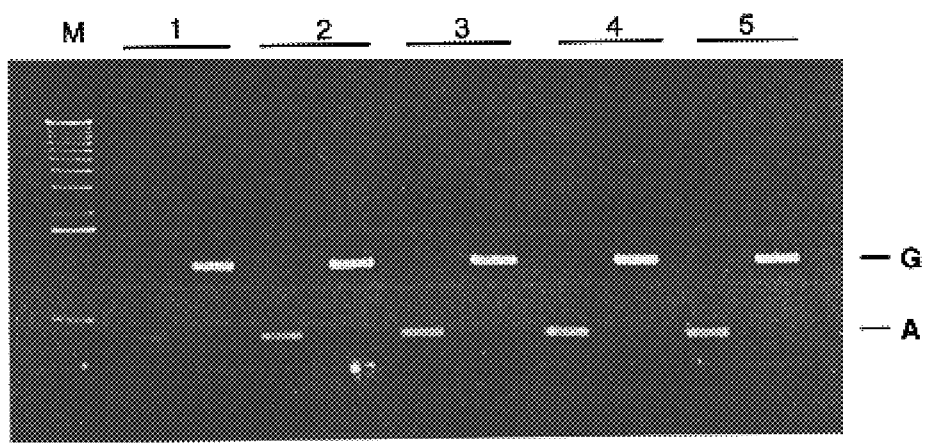

The inventor used the ATM gene to monitor the success of first strand synthesis. The ATM coding region is approximately 9 kb in length (Savitsky et al., 1995b) and PCR primers were prepared that could amplify various regions of the ATM cDNA (shown in FIG. 1A). As shown (FIG. 1B), the amount of PCR product derived from the ATM cDNA increases with each successive cycle of RT incubation. This is particularly true for the primers (pairs A1 and A2) that amplify regions that are nearest to the 5' end of the cDNA.

```
A1  TGC TTA TCT GCT GCC GTC AA          (seq id no:1)

A2  GCT CCG TTA ATA GCA CCA TTA GA      (seq id no:2)

G1  CTA TCC CAC ACT TAG CAG GTT         (seq id no:3)

G2  TGG AAT CTT CAT TCC GTC TCT         (seq id no:4)
```

Once second strand synthesis is performed (with E. coli polymerase I and Rnase H) and linkers are added to the cDNA by blunt-end ligation, a useful method to help insure that long cDNAs are represented in the library is to size fractionate the cDNA. This step removes the very small cDNAs that represent only fragments of complete transcripts. This also allows the long cDNAs to be ligated to the vector separately from the shorter species. In the case of plasmid vectors this is an important consideration since shorter molecules cyclize more efficiently than longer molecules (Legerski and Robberson, 1985), resulting in under-representation of the longer molecules in the library.

Figure 2:
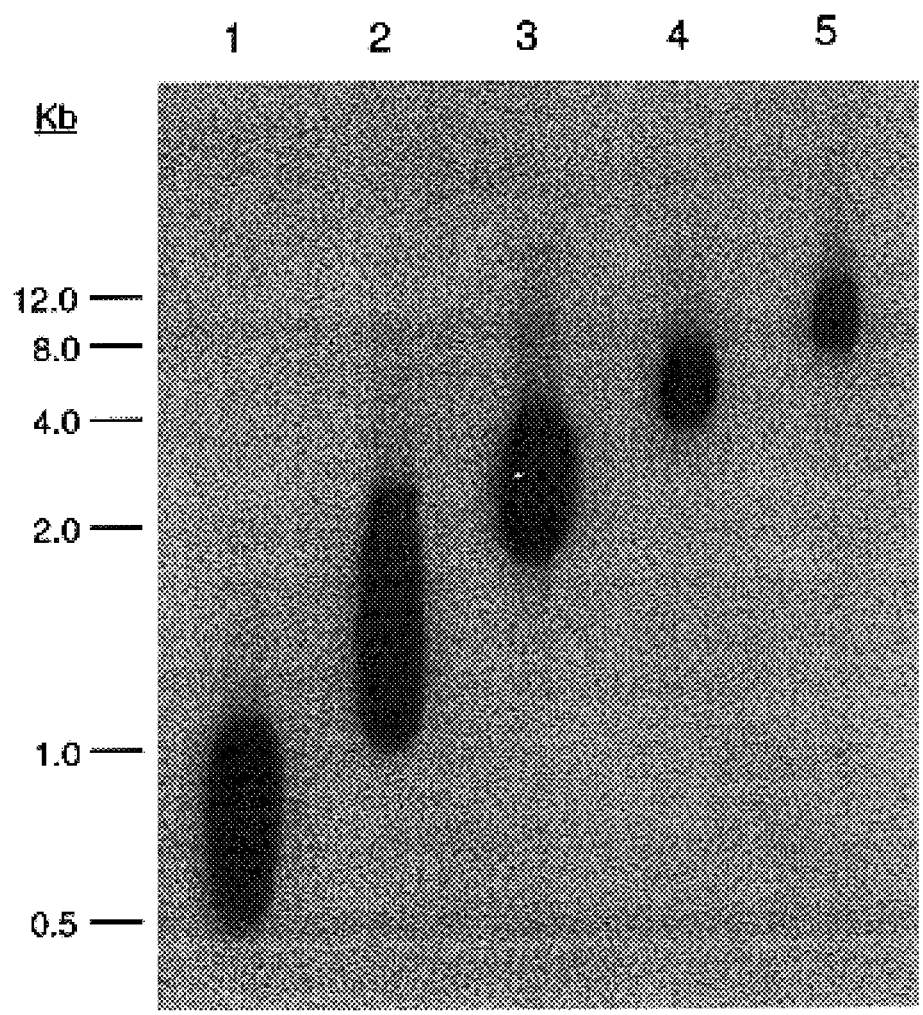
FIG. 2. Fractionation of HeLa cDNA (after second synthesis) by agarose gel electroporation. First strand synthesis was performed by three cycles of the dual RT procedure described in the text. Lane 1, 0.5–1 kb; lane 2, 1–2 kb; lane 3, 2–4 kb; lane 4, 4–8 kb; and lane5,>8 kb.

In the libraries previously made, the cDNA was fractionated by agarose gel electrophoresis and sub-libraries representative of particular size classes were made. This strategy was of great importance in the successes in isolating genes by expression cloning approaches (Legerski and Peterson, 1992; Tebbs et al., 1995; Henning et al., 1995). Shown in FIG. 2 is an example of the fractionation of cDNA (both first and second strand) produced by the dual RT cycling procedure described above. As indicated the fractionation procedure works well and demonstrates that even quite large cDNAs (above 10 kb) are present in the sample. Sublibraries can be prepared from each fraction and should be highly representational for each size class of cDNA.

EXAMPLE 3

Verification of Presence of full length cDNAs in a library

Two genes in addition to the ATM gene (Savitsky, 1995a; Savitsky, 1995b) that express long transcripts are the ATR gene (Bentley et al., 1996) (possible human homologue of S. pombe RAD3) at 8.2 kb and the DNA–PK (DNA dependent protein kinase) (Blast accession number u47077) gene at 13.5 kb. All three of these genes are ubiquitously expressed, thus making them good candidates for the evaluation of cDNAs from different tissues.

As with the ATM gene PCR primers that will allow specific amplification of segments of these genes particularly near end of the cDNAs can be prepared. Use of these PCR primers will allows determination whether full-length cDNAs for these genes have been synthesized and cloned into a library. By following all three cDNAs to insure that they are present in full-length form in a library should be a good indication that the library is representational for all cDNAs.

Another approach that can be used to examine the size of cDNAs is to perform Southern analysis after both first (for each cycle of RT synthesis) and second strand synthesis. These blots will be probed with the three genes described above. The Southern blot analysis will help to verify the PCR analysis, and in addition will yield information about the fraction of cDNA that is full-length for these three genes.

EXAMPLE 4

Tissue Acquisition and RNA Extraction from Colorectal Carcinoma

Primary and metastatic tumors are acquired from surgical pathology following surgical procedures. Surgical specimens are resected according to standard techniques and the operative specimens are immediately examined by a surgical pathologist. After examination by the surgical pathologist, a piece of tumor tissue is set aside for the laboratory.

In order to insure that the tissue used for these studies has a high level of tumor content, several measures are taken. First of all, pieces around the edges of the tumor tissue are removed, formalin fixed, and hematoxylin cosin stained slides are prepared to allow histological inspection of the tumor tissue to verify high tumor content of the specimen. Prior to nucleic acid extraction, the tissue is pulverized in dry ice to generate a homogeneous tumor preparation. From this, a small amount of this homogeneous preparation is set aside for DNA extraction.

Additionally, when nucleic acids are extracted from the tissue, both DNA and RNA are collected. The DNA can then be examined for LOH or microsatellite instability in the case of the HNPCC tumor. The detection of either LOH or microsatellite instability provides further assessment of the high tumor content in the tissue.

Total RNA is extracted as previously described (Ender et al., 1993). Poly A+ RNA is prepared as previously described by Frazier et al. (1990). The quality of RNA may be determined by northern blotting of the ATM gene. The following tissues will be used as the source of RNA: HNPCC carcinoma: adenoma (villous, tubular), metastasis; APC carcinoma: adenoma (villous, tubular), metastasis; sporadic carcinoma: adenoma (villous, tubular), metastasis. For adenomas, multiples have to be pooled. For adenocarcinomas, RNA is extracted from single adenocarcinomas for each clone bank.

Samples of grossly normal colonic mucosa are routinely taken 1–2 cm and at least 10 cm from the nearest gross encroachment of the tumor. These are labeled as "adjacent and "distant" mucosae, respectively. The distant samples is used for the preparation of libraries representing normal control tissue.

1. Acquisition of Adenomas

Currently, there is a large collection of sporadic adenomas that have been collected over the past two years, and are available for these studies. In addition, some adenomas are available from HNPCC patients and APC patients. However, it will be necessary to collect additional specimens to get a sufficient amount of RNA for preparation of the cDNA clone banks.

When broad mucosal masses are encountered, four biopsies of the mass may be obtained in addition to those required for routine diagnostic evaluation. In such cases, four biopsies are also be taken of the "transitional mucosa", i.e. that normal-appearing mucosa that is within 5 10 cm of the leading edge of the tumor mass. Finally, four biopsies are taken of remote (>20 cm from the tumor mass), normal-appearing mucosa. For each set of four biopsies, one biopsy is formalin-fixed and subjected to routine histological analysis and 3 are pooled and stored frozen until they are subjected to nucleic acid extraction.

The nucleic acids are then assayed for expression of EF-1G. For the routine histological analysis one each of the specimens of transitional and normal colonic mucosa is submitted for examination. The specimens are fixed in formalin and embedded in paraffin for histologic examination, mucin studies and collagen type IV immunohistochemistry. The results of these studies may be correlated with those of other studies.

When polyps are encountered, they are, of necessity, handled in the usual diagnostic/therapeutic manner. That is, polyps that are too large to be removed via polypectomy are subjected to multiple mucosal biopsies for diagnostic purposes. These typically are broad based villous adenomas that require surgical resection and commonly contain at least foci of microinvasive carcinoma. In these cases, an additional four biopsies of the tumor, "transitional mucosa", and remote mucosa are obtained as in the cases of more obviously cancer containing masses.

"Snareable polyps" or polypoid mucosal masses (probable adenomas at endoscopy) are subjected to endoscopic polypectomy whenever feasible as this is the standard handling of such lesions. By means of this approach, the entire tumor is removed in such a way as to facilitate critical histologic evaluation, with good orientation, and a therapeutic objective is achieved, namely the removal of tissue with high potential for eventual malignant transformation. Prior to retrieval of the polyp, the additional biopsies of normal-appearing "transitional" and remote mucosa is performed. The retrieved polyp is wetted with normal saline and submitted to pathologists for further handling (routine diagnostic evaluation and sections for EF-1G assay), as described in the sections above.

Small polyps that are not amenable to polypectomy are typically subjected to "hot biopsy" removal of the lesion.

Because the amount of tissue retrieved is inevitably small, it is not normally possible to submit sections for EF-1G assay. However, biopsies of the normal adjacent and remote mucosa can be performed.

From these tissues cDNA libraries are prepared as described herein above.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adler and Modrich, *J. Biol. Chem.*, 254:11605–11614, 1979.
An et al., *J Clin Microbiol*;33(4):860–867 1995.
Beaucage, and Lyer, *Tetrahedron*, 48:2223–2311, 1992
Bebenek and Kunkel, *Nucl. Acids Res.*, 17:5408, 1989.
Belkin and Jannasch, *Arch. Microbiol.*, 141:181–186, 1985.
Bentley et al., *EMBO J*. 15, 6641–6651, 1996.
Bicknell et al., *Current Biology* 6:1695–1697, 1996
Bronner et al., *Nature*, 368:258–261; 1994, 1994
Bussey, In: Herrera L, ed. *Familial adenomalous polyposis*. New York: Alan R. Liss:1–7, 1990
Chen et al., Mol Med. 1(2): 153–160, 1995.
Chomczynski and Sacchi, *Anal Biochem*. 162(1): 156–159, 1987
D'Alessio and Gerard, *Nucl. Acids Res.*, 16:1999–2014, 1988.
Dale et al., *Plasmid*, 13:31–40, 1985.
Donahue et al., *J. Biol. Chem*. 269: 8604–8609, 1994.
Eckert and Kunkel, *PCR Methods and Applications*, 1:17–24, 1991.
Efstratiadis et al., Cell 7, 279–287, 1976
Endcr et al., Molecular Carcinogenesis 7:18–20, 1993.
Engler et al., *J. Biol. Chem.*, 258:11165–11173, 1983.
EP No. 320 308
Fearon and Vogelstein, Cell 61, 759–767, 1990
Fishel et al., *Cell*, 75:1027–1038, 1993
Freifelder, *Physical Biochemistry Applications to Biochemistry and Molecular Biology*, 2nd ed. Wm. Freeman and Co., New York, N.Y., 1982.
Frohman, In: *PCR PROTOCOLS: A GUIDE TO METHODS AND APPLICATIONS*, Academic Press, N.Y., 1990;
Gillam et al., *J. Biol. Chem*. 253, 2532, 1978.
Gillam et al., *Nucleic Acids Res*. 6, 2973, 1979.
Gingeras et al., PCT Application WO 88/10315
Glison et al., Biochem 13 :263, 1974
Grippo and Richardson, *J. Biol. Chem.*, 246:6867–6873, 1971.
Gubler and Hoffmann, *Gene*, 25:263–269, 1983.
Gubler, *Methods Enzymol*., 152:330–335, 1987.
Hearne et al., *Trends Genet*, 8:288–294; 1992.
Henning et al., *Cell* 82, 555–564, 1995.
Holland, P., et al., *Proc. Natl. Acad. Sci. USA* 88:7276–7280, 1991
Hori et al., *J Biol. Chem.*, 254:11598–11604, 1979.
Houts et al., *J Virol.*, 29:517–522, 1979.
Hugh and Griffin, *PCR Technology*, 228–229, 1994.
Iiyy et al., *Biotechnique* 11:464, 1991.
Innis et al., PCR™ Protocols, Academic Press, Inc., San Diego Calif., 1990.
Itakura and Riggs, *Science* 209:1401–1405, 1980.
Itakura et al., *J Biol. Chem*. 250, 4592 1975
Jannasch et al., *Applied Environ. Microbiol.*, 58:3472–3481, 1992.
Jarvinen Gut; 33:357–360, 1992
Jass and Stewart, Gut; 33:783–786, 1992.
Kaledin et al., *Biokhimiia*. 46(9): 1576–1584, 1981
Khorana, *Science* 203, 614 1979
Kong et al., *J Biol. Chem.*, 268:1965–1975, 1993.
Kunkel et al., *Methods Enzymol.*, 154:367–382, 1987.
Kwoh et al., *Proc. Nat. Acad. Sci. USA*, 86: 1173, 1989.
Lawyer, et al., *J. Biol. Chem*. 264:6427–6437, 1989
Lawyer, et al., *PCR Meth. and Appl*. 2(4): 275–287, 1993
Leach et al., *Cell*, 75:1215–1225, 1993
Leader et al., *DNA* 5, 235–238, 1986
Legerski and Robberson, *J. Molec. Biol*. 181, 297–312, 1985
Legerski, and Peterson, *Nature* 359, 1992
Lengauer, et al., *Nature* 386, 623–626, 1997
Liang and Pardee, *Science*, 257:967–970, 1992.
Liang et al. *Nucleic Acids Res*. 22:5763–5764, 1994.
Liu et al., *Nature Genetics* 9:48–55; 1995.
Lockhart et al., *Nature Biotech.*, 14:1675–1680, 1996.
Lynch et al., *Dis Colon Rectum* 31:372–37; 1988.
Lynch et al., *Gastroenterology*; 104:1535–1549, 1993.
Maniatis et al., *Cell*, 8:163, 1976.
Markowitz et al., *Science* 268: 1336–1338, 1995.
Mattila et al., *NAR*, 19:4967–4973, 1991.
McClary et al., *J. DNA Sequencing Mapping*, 1(3): 173–180, 1991.
Mead et al., *BioTechniques*, 11(1): 76–87, 1991.
Meinkoth and Wahl, *Methods Enzymol*, 152:91–94, 1987.
Modrich and Richardson, *J. Biol. Chem.*, 250:5515–5522, 1975.
Mok et al., *Gynecol Oncol*. 52(2): 247–252, 1994
Mulvihill In: Ingall J R F, Mastromarino A J, eds. Prevention of hereditary large bowel cancer. New York: Alan R. Liss,:61–75, 1983
Murray and Kelley, *Molec. Gen. Genet*., 175:77–87, 1979.
Myers, T. W. and Gelfand, D. H. *Biochemistry* 30:7661–7666, 1991
Nordstrom et al., *J Biol. Chem.*, 256:3112–3117, 1981.
Ohara et al., *Proc. Nat'l Acad. Sci. USA*, 86: 5673–5677, 1989.
Okayama, and Berg, *Mol. Cell. Biol*. 2, 161–173, 1982
Papadopoulos et al., *Science*, 263:1625–1629, 1994
Papadopoulos et al., *Science*. 268(5219): 1915–1917, 1995
Perler et al., *Adv. Protein Chem*. 48:377–435, 1996
Perler et al., *Proc. Nat'l Acad. Sci. USA*, 89:5577, 1992.
Peterson, and Legerski, *Gene* 107, 279–284, 1991
Powell et al., *Nature*; 359:235–237, 1992
Promega: 1993. Protocols and Applications Guide (2nd edition), p58–61, Promega, Madison, USA.
Quirke et al., *Gut* 29:603–607, 1988.
Rampino et al., *Science*, 275(5302): 967–969, 1997
Ruttimann et al., *Eur J Biochem*. 149(1): 41–46, 1985
Sager et al., FASEB J. 7(10): 964–970, 1993.
Sambrook et al., In: *Molecular Cloning. A Laboratory Manual*, second edition, Cold Spring Harbor Laboratory, Cold Spring Harbor, N.Y., 1989.
Sanger et al., *Proc. Nat'l Acad. Sci. USA*, 74:5463–5467, 1977.
Savitsky et al., *Hum. Mol. Genet.* 4, 2025–2032. 1995b
Savitsky et al., *Science* 268, 1749–1753. 1995a
Schwabe et al., *Focus*, 20: 30–33, 1998
Shimoomaye et al., *Gene Anal. Techn.* 6: 25–28, 1989
Souza et al., *Nature Genetics* 14:255–257 1996.
Studier et al., *Methods Enzymol.*, 185:60–89, 1990.
Tabor and Struhl, In: *Current Protocols in Molecular Biology*, Ausubel et al. (Eds.), John Wiley and Sons, N.Y., pp 3.5.10–3.5.12, 1989.
Tanese and Goff, *Proc. Nat'l Acac. Sci. USA*, 85:1977, 1988.
Tebbs et al., *Proc. Natl. Acad. Sci., U.S.A.* 92, 6354 1995
Thibnodeau et al., *Science*, 260:816–819; 1993.
U.S. Pat. No. 5,428,148,
U.S. Pat. No. 5,554,744,
U.S. Pat. No. 5,574,146,
U.S. Pat. No. 5,602,244
Ullrich et al., *Science*, 196:1313, 1977
Walker et al., *Proc. Nat'l Acad. Sci. USA*, 89:392–396 1992.
Watson et al., *Cancer Res.* 54(17): 4598–4602, 1994
Weber *Genomics*; 7:524–530, 1990.
Welsh et al. *Nucleic Acids Res.* 20(19): 4965–4970, 1992
Wickens et al., *J Biol. Chem.* 253: 2471–2482, 1978
Wu et al., *Genomics*, 4:560, 1989.
Young, K., et al., *J. of Clinical Microbiology* 31 4:882–886 1993.

---

---

U.S. Pat. No. 4,704,362
U.S. Pat. No. 5,221,619
U.S. Pat. No. 5,583,013
U.S. Pat. No. 4,659,774,
U.S. Pat. No. 4,683,195,
U.S. Pat. No. 4,683,202
U.S. Pat. No. 4,800,159,
U.S. Pat. No. 4,816,571,
U.S. Pat. No. 4,883,750
U.S. Pat. No. 4,959,463,
U.S. Pat. No. 5,141,813,
U.S. Pat. No. 5,262,311
U.S. Pat. No. 5,264,566,

What is claimed is:

1. A method for the synthesis of cDNA comprising the steps of:
   (a) providing a reaction mixture comprising a poly (A)+ RNA, an oligonucleotide primer, dNTPs;
   (b) incubating said reaction mixture of step (a) with a highly processive enzyme composition having reverse transcriptase activity at a normal temperature range to allow first strand synthesis;
   (c) incubating said reaction mixture of step (b) with a thermostable enzyme composition having reverse transcriptase activity at a temperature that inhibits the presence of secondary mRNA structures to generate a first strand; and (d) adding said first strand to a reaction mixture for the synthesis of a second strand complementary to said first strand wherein said second strand synthesis reaction mixture comprises dNTPs and a DNA polymerase to initiate synthesis of said second strand and incubating said reaction mixture under conditions to allow the formation of a double-stranded cDNA, wherein said highly processive enzyme composition, said thermoststable enzyme composition, and said DNA polymerase are different enzymes.

2. The method of claim 1, wherein steps b and c are repeated.

3. The method of claim 2, wherein said steps b and c are repeated once.

4. The method of claim 2, wherein said steps b and c are repeated twice.

5. The method of claim 2, wherein said steps b and c are repeated three times.

6. The method of claim 1, wherein the reaction mixture of step (a) further comprises an RNase inhibitor.

7. The method of claim 1, wherein the second strand synthesis reaction mixture of step (d) further comprises DEPC-treated H20.

8. The method of claim 1, wherein the second strand synthesis reaction mixture of step (d) further comprises RNase H.

9. The method of claim 1, further comprising the step of amplifying said double-stranded cDNA molecule of step (d).

10. The method of claim 9, wherein the step of amplifying comprises PCR.

11. The method of claim 1, wherein the temperature of step (b) is between about 37° C. and about 43° C.

12. The method of claim 1, wherein the temperature of step (c) about 56° C. and about 95° C.

13. The method of claim 1, wherein said processive reverse transcriptase is selected from the group consisting of Superscript™; AMV Reverse Transcriptase, M-MLV Reverse Transcriptase.

14. The method of claim 1, wherein said thermostable reverse transcriptase is selected from the group consisting of RetrotherM™; Thermoscript™ and Tth reverse transcriptase.

15. The method of claim 1, wherein said DNA polymerase is thermostable.

16. The method of claim 1, wherein said DNA polymerase is selected from the group consisting of DNA Polymerase I, T4 DNA Polymerase, DNA Polymerase I Klenow fragment, PLATINUM taq™.

17. The method of claim 15, wherein said thermostable DNA polymerase is selected from the group consisting of Tfl DNA Polymerase, Taq DNA Polymerase, Tli DNA Polymerase, Tth DNA Polymerase, Vent™, Deepvent™ and pfu.

18. The method of claim 1, wherein said sample comprises between about 0.1 and picograms and 10 micrograms of polyA RNA.

19. The method of claim 1, further comprising the step of adding linkers to said double stranded cDNA.

20. The method of claim 19, wherein said linkers are added by blunt end ligation.

21. The method of claim 1, wherein said reaction mixture comprises between 1 and $10^8$ copies of said poly(A)+RNA.

22. The method of claim 1, wherein said poly(A)+RNA is from a tumor.

23. A method of increasing the length of cDNAs in a cDNA libraiy comprising the steps of:

(a) providing a reaction mixture comprising a poly (A)+ RNA, an oligonucleotide primer and dNTPs;

(b) incubating said reaction mixture of step (a) with a highly processive enzyme composition having reverse transcnrptase activity at a normal temperature range to allow first strand synthesis;

(c) incubating said reaction mixture of step (b) with a thermostable enzyme composition having reverse trariscriptase activity at a temperature that inhibits the presence of secondary mRNA structures to generate a first strand;

(d) adding said first strand to a reaction mixture for the synthesis of a second strand complementary to said first strand wherein said second strand synthesis reaction mixture comprises dNTPs and a DNA polymerase to initiate synthesis of said second strand and incubating said reaction mixture under conditions to allow the formation of double-stranded cDNA; and (e) amplifying said double-stranded cDNA of step (d)

wherein incubation at the temperatures in steps (c) inhibits the formation of secondary mRNA structures thereby resulting in cDNA species that are longer than in those produced in a normal temperature range, and wherein said highly processive enzyme composition, said thermosistable enzyme composition, and said DNA polymerase are different enzymes.

24. A method for the production of full length cDNAs comprising the steps of:

(a) providing a reaction mixture comprising a poly (A)+ RNA, an oligonucicotide primer and dNTPs;

(b) incubating said reaction mixture of step (a) with a highly processive enzyme composition having reverse transcriptase activity at a normal temperature range to allow first strand synthesis;

(c) incubating said reaction mixture of step (b) with a thermostable enzyme composition having reverse transcriptase activity at a temperature that inhibits the presence of secondary mRNA structures to generate a first strand;

(d) adding said first strand to a reaction mixture for the synthesis of a second strand complementary to said first strand wherein said second strand synthesis reaction mixture comprises dNTPs and a DNA polymerase to initiate synthesis of said second strand and incubating said reaction mixture under conditions to allow the formation of a double-stranded cDNA molecule, and (e) amplifying said double-stranded cDNA molecule of step (d)

wherein the inhibition of secondary structure formation in step (b) allows the production of long cDNA moieties, and wherein said highly processive enzyme composition, said thermoststable enzyme composition, and said DNA polymerase are different enzymes.

25. The method of claim 24, wherein said cDNA moiety has a size of between about 0.5 kB and 20 kB.

26. IThe method of claim 24, wherein said cDNA encodes a gene selected from the group consisting of XPC, CSA, XRCC3, XRCC2, XRCC9, ATM, ATR, RAD3, DNA-PK, ERCC1, XPA, XPB, XPC, XPD, XPF, XPG, CSB and HHR23B.

27. The method of claim 24, wherein said cDNA encodes a gene related to colorectal carcinoma.

28. The method of claim 27, wherein said colorectal carcinoma is hereditary colorectal carcinoma.

29. The method of claim 27, wherein said colorectal carcinoma is sporadic colorectal carcinoma.

30. The method of claim 28, wherein said gene is selected from the group consisting of hMSH2, hMLH1, hPMS1, hPMS2 and GTBP.

31. The method of claim 29, wherein said gene is selected from the group consisting of transforming growth factor b type II receptor, insulin-like growth factor II receptor, BAX and β2-microglobulin.

32. A method for synthesizing long cDNA moieties comprising the steps of
(a) providing a reaction mixture comprising a poly (A)+ RNA, an oligonucleotide primer and dNTPs,
(b) incubating said reaction mixture of step (a) with a highly processive enzyme composition having reverse transcriptase activity at a normal temperature range to allow first strand synthesis;
(c) incubating said reaction mixture of step (b) with a thermostable enzyme composition having reverse transcriplase activity at a temperature that inhibits the presence of secondary mRNA structures to generate a first strand;
(d) adding said first strand to a reaction mixture for the synthesis of a second strand complementary to said first strand wherein said second strand synthesis reaction mixture comprises dNTPs and a DNA polymerase to initiate synthesis of said second strand and incubating said reaction mixture under conditions to allow the formation of a double-stranded cDNA, and
(e) amplifying said double-stranded cDNA molecule of step (d)
wherein the inhibition of secondary structure formation in step (b) allows the production of cDNA moieties that are longer than those obtained when such secondary structure formation is not inhibited, and wherein said highly processive enzyme composition, said thermostsable enzyme composition, and said DNA polymerase are different enzymes.

33. A method for producing a library of cDNA species from a tumor comprising the steps of:
(a) providing a reaction mixture comprising a poly (A)+ RNA extracted from said tumor, an oligonucleotide primer and dNTPs;
(b) incubating said reaction mixture of step (a) with a highly processive enzyme composition having reverse transcriptase activity at a normal temperature range to allow first strand synthesis;
(c) incubating said reaction mixture of step (b) with a thermostable enzyme composition having reverse transcriptase activity at a temperature that inhibits the presence of secondary mRNA structures to generate a first strand;
(d) adding said first strand to a reaction mixture for the synthesis of a second strand complementary to said first strand wherein said second strand synthesis reaction mixture comprises dNTPs and a DNA polymerase to initiate synthesis of said second strand and incubating said reaction mixture under conditions to allow the formation of a double-stranded cDNA;
(e) amplifying said double-stranded cDNA molecule of step (d), and
(f) inserting said cDNA into an appropriate vector,
wherein said highly processive enzyme composition, said thermoststable enzyme composition, and said DNA polymerase are different enzymes.

34. The method of claim 33, wherein said tumor is a colorectal tumor.

* * * * *

UNITED STATES PATENT AND TRADEMARK OFFICE
CERTIFICATE OF CORRECTION

PATENT NO. : 6,406,891 B1
DATED : June 18, 2002
INVENTOR(S) : Legerski

It is certified that error appears in the above-identified patent and that said Letters Patent is hereby corrected as shown below:

Column 36,
Line 63, please delete "transcriptasc" and insert -- transcriptase -- therefor.

Column 37,
Line 11, please delete "thermoststable" and insert -- thermostable -- therefor.
Line 24, please delete "H2O" and insert -- $H_2O$ -- therefor.
Line 33, please delete "37º C." and insert -- 37 ºC. -- therefor.
Line 35, please delete "56º C." and insert -- 56 ºC. -- therefor.
Line 42, please delete "RetrotherM$^{TM}$" and insert -- Retrotherm$^{TM}$ -- therefor.
Line 67, please delete "libraiy" and insert -- library -- therefor.

Column 38,
Line 5, please delete "transcnrptase" and insert -- transcriptase -- therefor.
Line 25, please delete "thermoststable" and insert -- thermostable -- therefor.
Line 53, please delete "thermoststable" and insert -- thermostable -- therefor.
Line 57, please delete "IThe" and insert -- The -- therefor.

Column 39,
Line 33, please delete "thermoststable" and insert -- thermostable -- therefor.

Column 40,
Line 29, please delete "thermoststable" and insert -- thermostable -- therefor.

Signed and Sealed this

Eighth Day of October, 2002

Attest:

Attesting Officer

JAMES E. ROGAN
Director of the United States Patent and Trademark Office

SEQUENCE LISTING

<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
tgcttatctg ctgccgtcaa                                               20

<210> SEQ ID NO 2
<211> LENGTH: 23
<212> TYPE: DNA
<213> ORGANISM: Homo sapiens

<400> SEQUENCE: 2
gctccgtaaa tagcaccatt aga                                           23

<210> SEQ ID NO 3
<211> LENGTH: 21
<212> TYPE: DNA
<213> ORGANISM: Homo sapiens

<400> SEQUENCE: 3
ctatcccaca cttagcaggt t                                             21

<210> SEQ ID NO 4
<211> LENGTH: 21
<212> TYPE: DNA
<213> ORGANISM: Homo sapiens

<400> SEQUENCE: 4
tggaatcttc attccgtctc t                                             21